United States Patent
Mao et al.

(10) Patent No.: US 11,306,340 B2
(45) Date of Patent: Apr. 19, 2022

(54) BIOSYNTHETIC PRODUCTION OF STEVIOL GLYCOSIDE REBAUDIOSIDE D4 FROM REBAUDIOSIDE E

(71) Applicant: Conagen Inc., Bedford, MA (US)

(72) Inventors: Guohong Mao, Burlington, MA (US); Jacob Edward Vick, Cambridge, MA (US); Michael Batten, Westford, MA (US); Yang Luo, Wuxi Jiangsu (CN); Yilin Wu, Wuxi Jiangsu (CN); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 131 days.

(21) Appl. No.: 16/562,559

(22) Filed: Sep. 6, 2019

(65) Prior Publication Data

US 2020/0102588 A1    Apr. 2, 2020

Related U.S. Application Data

(63) Continuation of application No. PCT/US2017/064430, filed on Dec. 4, 2017.

(60) Provisional application No. 62/467,467, filed on Mar. 6, 2017.

(51) Int. Cl.
   *C12P 19/56* (2006.01)
   *C12N 1/20* (2006.01)
   *C12N 9/10* (2006.01)

(52) U.S. Cl.
   CPC ............ *C12P 19/56* (2013.01); *C12N 1/20* (2013.01); *C12N 9/1051* (2013.01); *C12Y 204/01013* (2013.01); *C12Y 204/01017* (2013.01)

(58) Field of Classification Search
   CPC .................. C12P 16/56; C12N 9/1051
   See application file for complete search history.

(56) References Cited

U.S. PATENT DOCUMENTS

| 2016/0208303 A1 | 7/2016 | Mao et al. |
| 2016/0251635 A1 | 9/2016 | Mao et al. |
| 2016/0298159 A1 | 10/2016 | Tao et al. |

FOREIGN PATENT DOCUMENTS

| CN | 103114099 | 5/2013 |
| WO | WO 2016/043926 | 3/2016 |
| WO | WO 2016/073740 | 5/2016 |
| WO | WO 2018/071744 | 4/2018 |

OTHER PUBLICATIONS

International Search Report and Written Opinion for Application No. PCT/US2017/064430 dated Mar. 8, 2018.
International Preliminary Report on Patentability for Application No. PCT/US2017/064430 dated Sep. 19, 2019.
Prakash et al., Bioconversion of rebaudioside I from rebaudioside A. Molecules. Oct. 28, 2014;19(11):17345-55. doi: 10.3390/molecules191117345.
EP 17899320.0, Dec. 11, 2020, Extended European Search Report.

*Primary Examiner* — Suzanne M Noakes
(74) *Attorney, Agent, or Firm* — Wolf, Greenfield & Sacks, P.C.; W. John Keyes

(57) ABSTRACT

The present invention relates, in some aspects, to the production of steviol glycoside rebaudioside D4 through the use of rebaudioside E. In some aspects, the invention relates to mutant CP1 enzymes, mutant HV1 enzymes as well as host cells and methods utilizing such enzymes, such as to produce rebaudioside D4.

15 Claims, 15 Drawing Sheets

Specification includes a Sequence Listing.

SEQUENCE LISTING

<160> NUMBER OF SEQ ID NOS: 14

<210> SEQ ID NO 1
<211> LENGTH: 458
<212> TYPE: PRT
<213> ORGANISM: Stevia rebaudiana

<400> SEQUENCE: 1

Met Glu Asn Lys Thr Glu Thr Thr Val Arg Arg Arg Arg Ile Ile

-continued

```
1               5                   10                  15
Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
 50                  55                  60

Phe Ile Leu Asp Asn Asp Pro Gln Asp Glu Arg Ile Ser Asn Leu Pro
 65                  70                  75                  80

Thr His Gly Pro Leu Ala Gly Met Arg Ile Pro Ile Ile Asn Glu His
                 85                  90                  95

Gly Ala Asp Glu Leu Arg Arg Glu Leu Glu Leu Met Leu Ala Ser
                100                 105                 110

Glu Glu Asp Glu Glu Val Ser Cys Leu Ile Thr Asp Ala Leu Trp Tyr
                115                 120                 125

Phe Ala Gln Ser Val Ala Asp Ser Leu Asn Leu Arg Arg Leu Val Leu
                130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
                195                 200                 205

Lys Gln Thr Lys Ala Ser Ser Gly Val Ile Trp Asn Ser Phe Lys Glu
                210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
                275                 280                 285

Glu Lys Asp Phe Leu Glu Ile Ala Arg Gly Leu Val Asp Ser Lys Gln
                290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
                370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430
```

-continued

```
Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 2
<211> LENGTH: 1377
<212> TYPE: DNA
<213> ORGANISM: Stevia rebaudiana

<400> SEQUENCE: 2
atggagaata agacagaaac aaccgtaaga cggaggcgga ggattatctt gttccctgta     60
ccatttcagg gccatattaa tccgatcctc aattagcaa acgtcctcta ctccaaggga    120
ttttcaataa caatcttcca tactaacttt aacaagccta aaacgagtaa ttatcctcac    180
tttacattca ggttcattct agacaacgac cctcaggatg agcgtatctc aaatttacct    240
acgcatggcc ccttggcagg tatgcgaata ccaataatca atgagcatgg agccgatgaa    300
ctccgtcgcg agttagagct tctcatgctc gcaagtgagg aagacgagga agtttcgtgc    360
ctaataactg atgcgctttg gtacttcgcc caatcagtcg cagactcact gaatctacgc    420
cgtttggtcc ttatgacaag ttcattattc aactttcacg cacatgtatc actgccgcaa    480
tttgacgagt tgggttacct ggacccggat gacaaaacgc gattggagga caagcgtcg    540 ggcttcccca tgctgaaagt caaagatatt aagagcgctt atagtaattg gcaaattctg    600
aaagaaattc tcggaaaaat gataaagcaa accaaagcgt cctctggagt aatctggaac    660
tccttcaagg agttagagga atctgaactt gaaacggtca tcagagaaat ccccgctccc    720
tcgttcttaa ttccactacc caagcacctt actgcaagta gcagttccct cctagatcat    780
gaccgaaccg tgtttcagtg gctggatcag caacccccgt cgtcagttct atatgtaagc    840
tttgggagta cttcggaagt ggatgaaaag gacttcttag agattgcgcg agggctcgtg    900
gatagcaaac agagcttcct gtgggtagtg agaccgggat tcgttaaggg ctcgacgtgg    960
gtcgagccgt tgccagatgg ttttctaggg gagagaggga gaatcgtgaa atgggttcca   1020
cagcaagagg ttttggctca cggagctata ggggcctttt ggaccactc tggttggaat   1080 tctactcttg aaagtgtctg tgaaggcgtt ccaatgatat tttctgattt tgggcttgac   1140
cagcctctaa acgtcgcta tatgtctgat gtgttgaagg ttggcgtgta cctggagaat   1200
ggttgggaaa gggggaaat tgccaacgcc atacgccggg taatggtgga cgaggaaggt   1260
gagtacatac gtcagaacgc tcgggtttta aaacaaaaag cggacgtcag ccttatgaag   1320
ggaggtagct cctatgaatc cctagaatcc ttggtaagct atatatcttc gttataa     1377

<210> SEQ ID NO 3
<211> LENGTH: 458
<212> TYPE: PRT
<213> ORGANISM: Artificial sequence
<220> FEATURE:
<223> OTHER INFORMATION: CP1

<400> SEQUENCE: 3

Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45
```

```
Leu Ile Pro Leu Pro Lys His Leu Thr Ala Ser Ser Ser Leu Leu
     50                  55                  60

Asp His Asp Arg Thr Val Phe Gln Trp Leu Asp Gln Gln Pro Pro Ser
 65                  70                  75                  80

Ser Val Leu Tyr Val Ser Phe Gly Ser Thr Ser Glu Val Asp Glu Lys
                 85                  90                  95

Asp Phe Leu Glu Ile Ala Arg Gly Leu Val Asp Ser Lys Gln Ser Phe
                100                 105                 110

Leu Trp Val Val Arg Pro Gly Phe Val Lys Gly Ser Thr Trp Val Glu
            115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
                180                 185                 190

Tyr Met Ser Asp Val Leu Lys Val Gly Val Tyr Leu Glu Asn Gly Trp
            195                 200                 205

Glu Arg Gly Glu Ile Ala Asn Ala Ile Arg Arg Val Met Val Asp Glu
    210                 215                 220

Glu Gly Glu Tyr Ile Arg Gln Asn Ala Arg Val Leu Lys Gln Lys Ala
225                 230                 235                 240

Asp Val Ser Leu Met Lys Gly Gly Ser Ser Tyr Glu Ser Leu Glu Ser
                245                 250                 255

Leu Val Ser Tyr Ile Ser Ser Leu Glu Asn Lys Thr Glu Thr Thr Val
            260                 265                 270

Arg Arg Arg Arg Arg Ile Ile Leu Phe Pro Val Pro Phe Gln Gly His
    275                 280                 285

Ile Asn Pro Ile Leu Gln Leu Ala Asn Val Leu Tyr Ser Lys Gly Phe
290                 295                 300

Ser Ile Thr Ile Phe His Thr Asn Phe Asn Lys Pro Lys Thr Ser Asn
305                 310                 315                 320

Tyr Pro His Phe Thr Phe Arg Phe Ile Leu Asp Asn Asp Pro Gln Asp
                325                 330                 335

Glu Arg Ile Ser Asn Leu Pro Thr His Gly Pro Leu Ala Gly Met Arg
                340                 345                 350

Ile Pro Ile Ile Asn Glu His Gly Ala Asp Glu Leu Arg Arg Glu Leu
            355                 360                 365

Glu Leu Leu Met Leu Ala Ser Glu Glu Asp Glu Glu Val Ser Cys Leu
    370                 375                 380

Ile Thr Asp Ala Leu Trp Tyr Phe Ala Gln Ser Val Ala Asp Ser Leu
385                 390                 395                 400

Asn Leu Arg Arg Leu Val Leu Met Thr Ser Ser Leu Phe Asn Phe His
                405                 410                 415

Ala His Val Ser Leu Pro Gln Phe Asp Glu Leu Gly Tyr Leu Asp Pro
                420                 425                 430

Asp Asp Lys Thr Arg Leu Glu Glu Gln Ala Ser Gly Phe Pro Met Leu
            435                 440                 445

Lys Val Lys Asp Ile Lys Ser Ala Tyr Ser
    450                 455
```

<210> SEQ ID NO 4
<211> LENGTH: 1377
<212> TYPE: DNA
<213> ORGANISM: Artificial sequence
<220> FEATURE:
<223> OTHER INFORMATION: CP1

<400> SEQUENCE: 4

```
atgaactggc aaatcctgaa agaaatcctg ggtaaaatga tcaaacaaac caaagcgtcg      60
tcgggcgtta tctggaactc cttcaaagaa ctggaagaat cagaactgga aaccgttatt     120
cgcgaaatcc cggctccgtc gttcctgatt ccgctgccga acatctgac cgcgagcagc     180
agcagcctgc tggatcacga ccgtacggtc tttcagtggc tggatcagca accgccgtca     240
tcggtgctgt atgtttcatt cggtagcacc tctgaagtcg atgaaaaaga ctttctggaa     300
atcgctcgcg gcctggtgga tagtaaacag tccttcctgt gggtggttcg tccgggtttt     360
gtgaaaggca gcacgtgggt tgaaccgctg ccggatggct tcctgggtga acgcggccgt     420
attgtcaaat gggtgccgca gcaagaagtg ctggcacatg tgctatcgg cgcgttttgg     480
acccactctg gttggaacag tacgctggaa tccgtttgcg aaggtgtccc gatgattttc     540
agcgattttg gcctggacca gccgctgaat gcccgctata tgtctgatgt tctgaaagtc     600
ggtgtgtacc tggaaaacgg ttgggaacgt ggcgaaattg cgaatgccat ccgtcgcgtt     660
atggtcgatg aagaaggcga atacattcgc cagaacgctc gtgtcctgaa caaaaaagcg     720
gacgtgagcc tgatgaaagg cggtagctct tatgaatcac tggaatcgct ggttagctac     780
atcagttccc tggaaaataa aaccgaaacc acggtgcgtc gccgtcgccg tattatcctg     840
ttcccggttc cgtttcaggg tcatattaac ccgatcctgc aactggcgaa tgttctgtat     900
tcaaaaggct tttcgatcac catcttccat acgaacttca caaaccgaa accagtaac     960
tacccgcact ttacgttccg ctttattctg gataacgacc cgcaggatga acgtatctcc    1020
aatctgccga cccacggccc gctggccggt atgcgcattc cgattatcaa tgaacacggt    1080
gcagatgaac tgcgccgtga actggaactg ctgatgctgg ccagtgaaga agatgaagaa    1140
gtgtcctgtc tgatcaccga cgcactgtgg tatttcgccc agagcgttgc agattctctg    1200
aacctgcgcc gtctggtcct gatgacgtca tcgctgttca ttttcatgc gcacgtttct    1260
ctgccgcaat tgatgaact gggctacctg gaccccggatg acaaaacccg tctggaagaa    1320
caagccagtg gttttccgat gctgaaagtc aaagacatta aatccgccta ttcgtaa       1377
```

<210> SEQ ID NO 5
<211> LENGTH: 425
<212> TYPE: PRT
<213> ORGANISM: Artificial sequence
<220> FEATURE:
<223> OTHER INFORMATION: GXT6

<400> SEQUENCE: 5

```
Met Thr Pro Pro Phe Gly Ser Glu Leu Ala Leu Pro Glu Thr Phe Leu
1               5                   10                  15

Met Gly Ala Ala Thr Ser Ala His Gln Val Glu Gly Asn Asn Ile Gly
            20                  25                  30

Ser Asp Trp Trp Glu Ile Glu His Arg Pro Asp Thr Phe Val Ala Gln
        35                  40                  45

Pro Ser Gly Asp Ala Ala Asp Ser Tyr His Arg Trp Pro Glu Asp Met
    50                  55                  60

Asp Leu Leu Ala Gly Leu Gly Phe Asn Ala Tyr Arg Phe Ser Ile Glu
```

```
                65                  70                  75                  80
        Trp Ala Arg Ile Glu Pro Glu Pro Gly Arg Ile Ser Arg Ala Ala Leu
                            85                  90                  95

Ala His Tyr Arg Ala Met Val Arg Gly Ala Leu Glu Arg Gly Leu Thr
                        100                 105                 110

Pro Leu Val Thr Leu His His Phe Thr Cys Pro Arg Trp Phe Ser Ala
                    115                 120                 125

Arg Gly Gly Trp Leu Ala Pro Asp Ala Ala Glu Thr Phe Thr Ala Tyr
                130                 135                 140

Ala Arg Thr Ala Ser Glu Val Gly Glu Gly Val Ser His Val Ala
        145                 150                 155                 160

Thr Ile Asn Glu Pro Asn Met Leu Ala His Met Tyr Thr Leu Arg Arg
                        165                 170                 175

Leu Ala Ala Glu His Gly Trp Ser Ala Leu Ala Glu Gly Arg Arg Ala
                    180                 185                 190

Gly Ala Ala Ala Phe Asp Pro Ala Ala Val Ala Pro Asp Arg Asp Val
                195                 200                 205

Thr Ala Ala Leu Ile Glu Ala His Arg Arg Ser Ala Val Val Leu Arg
        210                 215                 220

Gln Ala Gly Leu Gln Val Gly Trp Thr Val Ala Asn Gln Val Tyr His
        225                 230                 235                 240

Ala Glu Pro Gly Ala Glu Glu Ile Ala Thr Ala Tyr Ala Arg Pro Arg
                        245                 250                 255

Glu Asp Val Phe Leu Glu Ala Ala Arg Glu Asp Asp Trp Ile Gly Val
                    260                 265                 270

Gln Ala Tyr Thr Arg His Arg Ile Gly Pro Asp Gly Pro Leu Pro Val
                275                 280                 285

Pro Asp Gly Ala Pro Thr Thr Leu Thr Gly Trp Glu Val Tyr Pro Asp
                290                 295                 300

Ala Leu Ala Glu Ala Val Leu His Thr Val Ala Thr Val Gly Ala Gln
        305                 310                 315                 320

Val Pro Val Ile Val Thr Glu Asn Gly Ile Ala Thr Gly Asp Asp Asp
                        325                 330                 335

Gln Arg Ile Ala Tyr Thr Arg Gln Ala Leu Ala Gly Leu Ala Arg Val
                    340                 345                 350

Met Arg Glu Gly Ala Asp Val Arg Gly Tyr Phe His Trp Ser Ala Leu
                355                 360                 365

Asp Asn Tyr Glu Trp Gly Thr Tyr Arg Pro Thr Phe Gly Leu Ile Gly
                370                 375                 380

Val Asp Pro Asp Thr Phe Ala Arg Thr Pro Lys Pro Ser Ala Arg Trp
        385                 390                 395                 400

Leu Gly Ala Leu Ala Arg Asp Arg Arg Leu Pro Ala Ala Lys Ala Pro
                        405                 410                 415

Val Gly Thr Gly Ala Pro Thr Ala Arg
                    420                 425

<210> SEQ ID NO 6
<211> LENGTH: 1275
<212> TYPE: DNA
<213> ORGANISM: Artificial sequence
<220> FEATURE:
<223> OTHER INFORMATION: GXT6

<400> SEQUENCE: 6
atgaccccac cgtttggtag cgaactggcg cttccggaaa cattccttat gggtgcggcc        60
```

```
acttcagctc accaggttga aggtaataat atcggtagcg attggtggga aattgagcac      120
cgcccggata cttttgttgc tcagccgtcc ggagatgcgg cagattccta tcaccgctgg      180
ccggaagata tggatttgct tgccggattg gctttaatg cttatcgttt tagtattgag       240
tgggctcgta ttgaaccgga acctggtcgg atttcaagag cggctctggc cattatcgt       300 gcgatggtcc gcggagcgct ggagcgtggc ctgacaccat tagtaactt gcatcacttt       360 acatgcccac ggtggttttc agctcggggc ggttggttag ctccagatgc agcggaaact     420
tttactgctt atgccagaac tgccagcgag gtagttggtg agggcgtgtc tcatgtcgcg     480
acgatcaacg agcctaacat gctggcacat atgtatactt tgagaagact tgcagcggaa    540
cacggttggt cagccttagc ggaaggaaga cgtgctggcg ccgcagcttt tgatccggct    600
gctgttgccc cggatcgcga tgtgacggct gctctgattg aggcgcaccg tcgcagcgcc    660
gtagtgctgc gccaggccgg cctgcaggtt ggctggacag ttgccaatca ggtttatcac    720
gccgaaccgg gagcagaaga aattgctacg gcctatgctc ggccacggga ggatgtattc    780
ttggaggcag cccgcgaaga tgattggatc ggcgtgcagg catatactcg tcaccgtatt    840
ggaccggatg gacctctgcc ggtacctgat ggggcaccta caacacttac tggctgggaa   900
gtttatcctg atgcccttgc agaagccgtg ctgcatacag tcgccaccgt gggtgcgcag   960
gtaccagtta ttgtaacaga gaatggtatc gccaccggcg atgatgatca gcgtatcgca  1020
tatactagac aggcactggc agggttggcc cgtgtcatgc gcgaaggtgc ggatgtgcgg  1080
ggatattttc attggtccgc attagataac tatgaatggg gcacctatcg tccaaccttc  1140
gggttaatcg gggttgatcc ggatacgttt gctcggacgc taaaccttc tgcacgctgg    1200 ctgggtgctc tggcacgcga tcgcagactg ccagccgcga aagcgcctgt cggcactggc   1260 gccctacag ctcgc                                                      1275
```

<210> SEQ ID NO 7
<211> LENGTH: 458
<212> TYPE: PRT
<213> ORGANISM: Artificial sequence
<220> FEATURE:
<223> OTHER INFORMATION: C1m2

<400> SEQUENCE: 7

```
Met Asn Trp Gln Ile Ala Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Ser
65                  70                  75                  80

Ser Val Leu Tyr Val Ser Phe Gly Ser Thr Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140
```

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
            165                 170                 175

Pro Met Ile Phe Ser Asp Phe Gly Gly Asp Gln Pro Leu Asn Ala Arg
        180                 185                 190

Tyr Met Ser Asp Val Leu Lys Val Gly Val Tyr Leu Glu Asn Gly Trp
    195                 200                 205

Glu Arg Gly Glu Ile Ala Asn Ala Ile Arg Arg Val Met Val Asp Glu
210                 215                 220

Glu Gly Glu Tyr Ile Arg Gln Asn Ala Arg Val Leu Lys Gln Lys Ala
225                 230                 235                 240

Asp Val Ser Leu Met Lys Gly Gly Ser Ser Tyr Glu Ser Leu Glu Ser
            245                 250                 255

Leu Val Ser Tyr Ile Ser Ser Leu Glu Asn Lys Thr Glu Thr Thr Val
        260                 265                 270

Arg Arg Arg Arg Arg Ile Ile Leu Phe Pro Val Pro Phe Gln Gly His
    275                 280                 285

Ile Asn Pro Ile Leu Gln Leu Ala Asn Val Leu Tyr Ser Lys Gly Phe
290                 295                 300

Ser Ile Thr Ile Phe His Thr Asn Phe Asn Lys Pro Lys Thr Ser Asn
305                 310                 315                 320

Tyr Pro His Phe Thr Phe Arg Phe Ile Leu Asp Asn Asp Pro Gln Asp
            325                 330                 335

Glu Arg Ile Ser Asn Leu Pro Thr His Gly Pro Leu Ala Gly Met Arg
        340                 345                 350

Ile Pro Ile Ile Asn Glu His Gly Ala Asp Glu Leu Arg Arg Glu Leu
    355                 360                 365

Glu Leu Leu Met Leu Ala Ser Glu Gly Asp Glu Val Ser Cys Leu
370                 375                 380

Ile Thr Asp Ala Leu Trp Tyr Phe Ala Gln Ser Val Ala Asp Ser Leu
385                 390                 395                 400

Asn Leu Arg Arg Leu Val Leu Met Thr Ser Ser Leu Phe Asn Phe His
            405                 410                 415

Ala His Val Ser Leu Pro Gln Phe Asp Glu Leu Gly Tyr Leu Asp Pro
        420                 425                 430

Asp Asp Lys Thr Arg Leu Glu Glu Gln Ala Ser Gly Phe Pro Met Leu
    435                 440                 445

Lys Val Lys Asp Ile Lys Ser Ala Tyr Ser
    450                 455

<210> SEQ ID NO 8
<211> LENGTH: 1377
<212> TYPE: DNA
<213> ORGANISM: Artificial sequence
<220> FEATURE:
<223> OTHER INFORMATION: C1m2

<400> SEQUENCE: 8
atgaactggc aaatcgcgaa agaaatcctg ggtaaaatga tcaaacaaac caaagcgtcg      60
tcgggcgtta tctggaactc cttcaaagaa ctggaagaat cagaactgga aaccgttatt     120
cgcgaaatcc cggctccgtc gttcctgatt ccgctgccga acatctgac cgcgagcagc     180 agcagcctgc tggatcacga ccgtacggtc tttcagtggc tggatcagca accgccgtca     240

-continued

```
tcggtgctgt atgtttcatt cggtagcacc tctgaagtcg atgaaaaaga ctttctggaa    300
atcgctcgcg gcctggtgga tagtaaacag tccttcctgt gggtggttcg tccgggtttt    360
gtgaaaggca gcacgtgggt tgaaccgctg ccggatggct tcctgggtga acgcggccgt    420
attgtcaaat gggtgccgca gcaagaagtg ctggcacatg gtgctatcgg cgcgttttgg    480
acccactctg gttggaacag tacgctggaa tccgtttgcg aaggtgtccc gatgattttc    540
agcgattttg gcggcgacca gccgctgaat gcccgctata tgtctgatgt tctgaaagtc    600
ggtgtgtacc tggaaaacgg ttgggaacgt ggcgaaattg cgaatgccat ccgtcgcgtt    660
atggtcgatg aagaaggcga atacattcgc cagaacgctc gtgtcctgaa acaaaaagcg    720
gacgtgagcc tgatgaaagg cggtagctct tatgaatcac tggaatcgct ggttagctac    780
atcagttccc tggaaaataa aaccgaaacc acggtgcgtc gccgtcgccg tattatcctg    840
ttcccggttc cgtttcaggg tcatattaac ccgatcctgc aactggcgaa tgttctgtat    900
tcaaaaggct tttcgatcac catcttccat acgaacttca acaaaccgaa aaccagtaac    960
tacccgcact ttacgttccg ctttattctg ataacgaccc gcaggatga acgtatctcc    1020
aatctgccga cccacggccc gctggccggt atgcgcattc cgattatcaa tgaacacggt    1080
gcagatgaac tgcgccgtga actggaactg ctgatgctgg ccagtgaaga agatgaagaa    1140
gtgtcctgtc tgatcaccga cgcactgtgg tatttcgccc agagcgttgc agattctctg    1200
aacctgcgcc gtctggtcct gatgacgtca tcgctgttca tttttcatgc gcacgtttct    1260
ctgccgcaat ttgatgaact gggctacctg gacccggatg acaaaacccg tctggaagaa    1320
caagccagtg ttttccgat gctgaaagtc aaagacatta aatccgccta ttcgtaa      1377
```

<210> SEQ ID NO 9
<211> LENGTH: 458
<212> TYPE: PRT
<213> ORGANISM: Artificial sequence
<220> FEATURE:
<223> OTHER INFORMATION: C1m3

<400> SEQUENCE: 9

```
Met Asn Trp Gln Ile Ala Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Ser
65                  70                  75                  80

Ser Val Leu Tyr Val Ser Phe Gly Ser Ala Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
```

|     |     |     |     |     | 165 |     |     |     | 170 |     |     |     |     | 175 |
| --- | --- | --- | --- | --- | --- | --- | --- | --- | --- | --- | --- | --- | --- | --- |
| Pro | Met | Ile | Phe | Ser | Asp | Phe | Gly | Gly | Asp | Gln | Pro | Leu | Asn | Ala | Arg |
|     |     |     | 180 |     |     |     |     | 185 |     |     |     | 190 |

Tyr Met Ser Asp Val Leu Lys Val Gly Val Tyr Leu Glu Asn Gly Trp
        195                200              205

Glu Arg Gly Glu Ile Ala Asn Ala Ile Arg Arg Val Met Val Asp Glu
      210              215              220

Glu Gly Glu Tyr Ile Arg Gln Asn Ala Arg Val Leu Lys Gln Lys Ala
225              230              235              240

Asp Val Ser Leu Met Lys Gly Gly Ser Ser Tyr Glu Ser Leu Glu Ser
            245              250              255

Leu Val Ser Tyr Ile Ser Ser Leu Glu Asn Lys Thr Glu Thr Thr Val
        260              265              270

Arg Arg Arg Arg Ile Ile Leu Phe Pro Val Pro Phe Gln Gly His
    275              280              285

Ile Asn Pro Ile Leu Gln Leu Ala Asn Val Leu Tyr Ser Lys Gly Phe
    290              295              300

Ser Ile Thr Ile Phe His Thr Asn Phe Asn Lys Pro Lys Thr Ser Asn
305              310              315              320

Tyr Pro His Phe Thr Phe Arg Phe Ile Leu Asp Asn Asp Pro Gln Asp
            325              330              335

Glu Arg Ile Ser Asn Leu Pro Thr His Gly Pro Leu Ala Gly Met Arg
        340              345              350

Ile Pro Ile Ile Asn Glu His Gly Ala Asp Glu Leu Arg Arg Glu Leu
    355              360              365

Glu Leu Leu Met Leu Ala Ser Glu Glu Asp Glu Val Ser Cys Leu
    370              375              380

Ile Thr Asp Ala Leu Trp Tyr Phe Ala Gln Ser Val Ala Asp Ser Leu
385              390              395              400

Asn Leu Arg Arg Leu Val Leu Met Thr Ser Ser Leu Phe Asn Phe His
            405              410              415

Ala His Val Ser Leu Pro Gln Phe Asp Glu Leu Gly Tyr Leu Asp Pro
        420              425              430

Asp Asp Lys Thr Arg Leu Glu Glu Gln Ala Ser Gly Phe Pro Met Leu
        435              440              445

Lys Val Lys Asp Ile Lys Ser Ala Tyr Ser
    450              455

<210> SEQ ID NO 10
<211> LENGTH: 1377
<212> TYPE: DNA
<213> ORGANISM: Artificial sequence
<220> FEATURE:
<223> OTHER INFORMATION: C1m3

<400> SEQUENCE: 10

```
atgaactggc aaatcgcgaa agaaatcctg ggtaaaatga tcaaacaaac caaagcgtcg    60
tcgggcgtta tctggaactc cttcaaagaa ctggaagaat cagaactgga aaccgttatt   120
cgcgaaatcc cggctccgtc gttcctgatt ccgctgccga acatctgac cgcgagcagc   180 agcagcctgc tggatcacga ccgtacggtc tttcagtggc tggatcagca accgccgtca   240
tcggtgctgt atgtttcatt cggtagcgcc tctgaagtcg atgaaaaaga ctttctggaa   300
atcgctcgcg gcctggtgga tagtaaacag tccttcctgt gggtggttcg tccgggtttt   360
gtgaaaggca gcacgtgggt tgaaccgctg ccggatggct tcctgggtga acgcggccgt   420
```

```
attgtcaaat gggtgccgca gcaagaagtg ctggcacatg gtgctatcgg cgcgttttgg    480
acccactctg gttggaacag tacgctggaa tccgtttgcg aaggtgtccc gatgattttc    540
agcgattttg gcggcgacca gccgctgaat gcccgctata tgtctgatgt tctgaaagtc    600
ggtgtgtacc tggaaaacgg ttgggaacgt ggcgaaattg cgaatgccat ccgtcgcgtt    660
atggtcgatg aagaaggcga atacattcgc cagaacgctc gtgtcctgaa acaaaaagcg    720
gacgtgagcc tgatgaaagg cggtagctct tatgaatcac tggaatcgct ggttagctac    780
atcagttccc tggaaaataa aaccgaaacc acggtgcgtc gccgtcgccg tattatcctg    840
ttcccggttc cgtttcaggg tcatattaac ccgatcctgc aactggcgaa tgttctgtat    900
tcaaaaggct tttcgatcac catcttccat acgaacttca acaaaccgaa accagtaac    960
tacccgcact ttacgttccg ctttattctg gataacgacc cgcaggatga acgtatctcc   1020
aatctgccga cccacggccc gctggccggt atgcgcattc cgattatcaa tgaacacggt   1080
gcagatgaac tgcgccgtga actggaactg ctgatgctgg ccagtgaaga agatgaagaa   1140
gtgtcctgtc tgatcaccga cgcactgtgg tatttcgccc agagcgttgc agattctctg   1200
aacctgcgcc gtctggtcct gatgacgtca tcgctgttca attttcatgc gcacgtttct   1260
ctgccgcaat tgatgaact gggctacctg acccggatg acaaaacccg tctggaagaa    1320
caagccagtg ttttccgat gctgaaagtc aaagacatta atccgccta ttcgtaa       1377
```

<210> SEQ ID NO 11
<211> LENGTH: 459
<212> TYPE: PRT
<213> ORGANISM: Hordeum vulgare

<400> SEQUENCE: 11

```
Met Asp Gly Asn Ser Ser Ser Pro Leu His Val Ile Cys Pro
1               5                  10                  15

Trp Leu Ala Leu Gly His Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205
```

```
Met Arg Ser Asp Leu Val Ala Ile Arg Ser Cys Ala Glu Trp Glu Pro
    210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
                260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335

Val Pro Gln Ile Gly Val Leu Ala His Gly Ala Val Ala Ala Phe Leu
                340                 345                 350

Thr His Cys Gly Trp Asn Ser Thr Ile Glu Gly Leu Leu Phe Gly His
        355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
                405                 410                 415

Ala Val Glu Glu Asp Gly Arg Arg Val Phe Thr Ala Asn Ala Lys Lys
                420                 425                 430

Met Gln Glu Ile Val Ala Asp Gly Ala Cys His Glu Arg Cys Ile Asp
        435                 440                 445

Gly Phe Ile Gln Gln Leu Arg Ser Tyr Lys Ala
    450                 455

<210> SEQ ID NO 12
<211> LENGTH: 1380
<212> TYPE: DNA
<213> ORGANISM: Hordeum vulgare

<400> SEQUENCE: 12
atggatggta actcctcctc ctcgccgctg catgtggtca tttgtccgtg gctggctctg      60
ggtcacctgc tgccgtgtct ggatattgct gaacgtctgg cgtcacgcgg ccatcgtgtc     120
agttttgtgt ccaccccgcg caacattgcc cgtctgccgc cgctgcgtcc ggctgttgca     180
ccgctggttg atttcgtcgc actgccgctg ccgcatgttg acggtctgcc ggagggtgcg     240
gaatcgacca tgatgtgcc gtatgacaaa tttgaactgc accgtaaggc gttcgatggt     300
ctggcggccc cgtttagcga atttctgcgt gcagcttgcg cagaaggtgc aggttctcgc     360
ccggattggc tgattgtgga cacctttcat cactgggcgg cggcggcggc ggtggaaaac     420
aaagtgccgt gtgttatgct gctgctgggt gcagcaacgg tgatcgctgg tttcgcgcgt     480
ggtgttagcg aacatgcggc ggcggcggtg ggtaaagaac gtccggctgc ggaagccccg     540
agttttgaaa ccgaacgtcg caagctgatg accacgcaga atgcctccgg catgaccgtg     600
gcagaacgct atttcctgac gctgatgcgt agcgatctgg ttgccatccg ctcttgcgca     660
```

```
gaatgggaac cggaaagcgt ggcagcactg accacgctgg caggtaaacc ggtggttccg    720
ctgggtctgc tgccgccgag tccggaaggc ggtcgtggcg tttccaaaga agatgctgcg    780
gtccgttggc tggacgcaca gccggcaaag tcagtcgtgt acgtcgcact gggttcggaa    840
gtgccgctgc gtgcggaaca agttcacgaa ctggcactgg gcctggaact gagcggtgct    900
cgctttctgt gggcgctgcg taaaccgacc gatgcaccgg acgccgcagt gctgccgccg    960
ggtttcgaag aacgtacccg cggccgtggt ctggttgtca cgggttgggt gccgcagatt   1020
ggcgttctgg ctcatggtgc ggtggctgcg tttctgaccc actgtggctg gaactctacg   1080
atcgaaggcc tgctgttcgg tcatccgctg attatgctgc cgatcagctc tgatcagggt   1140
ccgaatgcgc gcctgatgga aggccgtaaa gtcggtatgc aagtgccgcg tgatgaatca   1200
gacggctcgt ttcgtcgcga agatgttgcc gcaaccgtcc gcgccgtggc agttgaagaa   1260
gacggtcgtc gcgtcttcac ggctaacgcg aaaaagatgc aagaaattgt ggccgatggc   1320
gcatgccacg aacgttgtat tgacggtttt atccagcaac tgcgcagtta caaggcgtaa   1380
```

<210> SEQ ID NO 13
<211> LENGTH: 458
<212> TYPE: PRT
<213> ORGANISM: Artificial sequence
<220> FEATURE:
<223> OTHER INFORMATION: CR1

<400> SEQUENCE: 13

```
Met Asn Trp Gln Ile Ala Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Leu Leu
    50                  55                  60

Asp His Asp Arg Thr Val Phe Gln Trp Leu Asp Gln Gln Pro Pro Ser
65                  70                  75                  80

Ser Val Leu Tyr Val Ser Phe Gly Ser Thr Ser Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
            180                 185                 190

Tyr Met Ser Asp Val Leu Lys Val Gly Val Tyr Leu Glu Asn Gly Trp
        195                 200                 205

Glu Arg Gly Glu Ile Ala Asn Ala Ile Arg Arg Val Met Val Asp Glu
    210                 215                 220

Glu Gly Glu Tyr Ile Arg Gln Asn Ala Arg Val Leu Lys Gln Lys Ala
225                 230                 235                 240
```

Asp Val Ser Leu Met Lys Gly Gly Ser Ser Tyr Glu Ser Leu Glu Ser
            245                 250                 255

Leu Val Ser Tyr Ile Ser Ser Leu Glu Asn Lys Thr Glu Thr Thr Val
        260                 265                 270

Arg Arg Arg Arg Ile Ile Leu Phe Pro Val Pro Phe Gln Gly His
    275                 280                 285

Ile Asn Pro Ile Leu Gln Leu Ala Asn Val Leu Tyr Ser Lys Gly Phe
    290                 295                 300

Ser Ile Thr Ile Phe His Thr Asn Phe Asn Lys Pro Lys Thr Ser Asn
305                 310                 315                 320

Tyr Pro His Phe Thr Phe Arg Phe Ile Leu Asp Asn Asp Pro Gln Asp
                325                 330                 335

Glu Arg Ile Ser Asn Leu Pro Thr His Gly Pro Leu Ala Gly Met Arg
            340                 345                 350

Ile Pro Ile Ile Asn Glu His Gly Ala Asp Glu Leu Arg Arg Glu Leu
        355                 360                 365

Glu Leu Leu Met Leu Ala Ser Glu Glu Asp Glu Val Ser Cys Leu
    370                 375                 380

Ile Thr Asp Ala Leu Trp Tyr Phe Ala Gln Ser Val Ala Asp Ser Leu
385                 390                 395                 400

Asn Leu Arg Arg Leu Val Leu Met Thr Ser Ser Leu Phe Asn Phe His
                405                 410                 415

Ala His Val Ser Leu Pro Gln Phe Asp Glu Leu Gly Tyr Leu Asp Pro
            420                 425                 430

Asp Asp Lys Thr Arg Leu Glu Glu Gln Ala Ser Gly Phe Pro Met Leu
        435                 440                 445

Lys Val Lys Asp Ile Lys Ser Ala Tyr Ser
    450                 455

<210> SEQ ID NO 14
<211> LENGTH: 1377
<212> TYPE: DNA
<213> ORGANISM: Artificial sequence
<220> FEATURE:
<223> OTHER INFORMATION: CR1

<400> SEQUENCE: 14
atgaactggc aaatcgcgaa agaaatcctg ggtaaaatga tcaaacaaac caaagcgtcg      60
tcgggcgtta tctggaactc cttcaaagaa ctggaagaat cagaactgga aaccgttatt     120
cgcgaaatcc cggctccgtc gttcctgatt ccgctgccga acatctgac cgcgagcagc      180 agcagcctgc tggatcacga ccgtacggtc tttcagtggc tggatcagca accgccgtca     240
tcggtgctgt atgtttcatt cggtagcacc tctgaagtcg atgaaaaaga ctttctggaa     300
atcgctcgcg gcctggtgga tagtaaacag tccttcctgt gggtggttcg tccgggtttt     360
gtgaaaggca gcacgtgggt tgaaccgctg ccggatggct tcctgggtga acgcggccgt     420
attgtcaaat gggtgccgca gcaagaagtg ctggcacatg tgctatcgg cgcgttttgg     480 acccactctg gttggaacag tacgctggaa tccgtttgcg aaggtgtccc gatgattttc     540
agcgactttg cctggaccca gccgctgaat gcccgctata tgtctgatgt ctgaaagtc      600 ggtgtgtacc tggaaaacgg ttgggaacgt ggcgaaattg cgaatgccat ccgtcgcgtt     660
atggtcgatg aagaaggcga atacattcgc cagaacgctc gtgtcctgaa acaaaaagcg     720
gacgtgagcc tgatgaaagg cggtagctct tatgaatcac tggaatcgct ggttagctac     780
atcagttccc tggaaaataa aaccgaaacc acggtgcgtc gccgtcgccg tattatcctg     840

```
ttcccggttc cgtttcaggg tcatattaac ccgatcctgc aactggcgaa tgttctgtat    900
tcaaaaggct tttcgatcac catcttccat acgaacttca acaaaccgaa aaccagtaac    960
tacccgcact ttacgttccg ctttattctg gataacgacc cgcaggatga acgtatctcc   1020
aatctgccga cccacggccc gctggccggt atgcgcattc cgattatcaa tgaacacggt   1080
gcagatgaac tgcgccgtga actggaactg ctgatgctgg ccagtgaaga agatgaagaa   1140
gtgtcctgtc tgatcaccga cgcactgtgg tatttcgccc agagcgttgc agattctctg   1200
aacctgcgcc gtctggtcct gatgacgtca tcgctgttca attttcatgc gcacgtttct   1260
ctgccgcaat ttgatgaact gggctacctg gacccggatg acaaaacccg tctggaagaa   1320
caagccagtg gtttccgat gctgaaagtc aaagacatta aatccgccta ttcgtaa      1377
```

BIOSYNTHETIC PRODUCTION OF STEVIOL GLYCOSIDE REBAUDIOSIDE D4 FROM REBAUDIOSIDE E

CROSS-REFERENCE TO RELATED APPLICATIONS

This application is a continuation of International Application No. PCT/US2017/064430, filed on Dec. 4, 2017, which claims priority to U.S. Provisional Application No. 62/467,467, filed on Mar. 6, 2017, the contents of each of which are incorporated by reference herein in their entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 6, 2019 is named C149770025US01-SEQ-ZJG and is 41,155 bytes in size.

FIELD OF THE INVENTION

The field of the invention relates to methods and processes useful in the production of a specific steviol glycoside via a biosynthetic pathway engineered into selected microorganisms. More specifically, the present disclosure relates to the production of a previously unknown rebaudioside, rebaudioside D4 ("Reb D4") that can be synthesized from Rebaudioside E ("Reb E") via enzymatic conversion.

BACKGROUND OF THE INVENTION

Several steviol glycosides were found as compounds in *Stevia rebaudiana* leaves, and have been widely used as high intensity, low-calorie sweeteners in food, feed and beverages. These naturally occurring steviol glycosides have the same basic diterpene structure (steviol backbone) but differ in the number and structure of their carbohydrate residue modifications (e.g. glucose, rhamnose, and xylose residues) at the C13 and C19 positions of the steviol backbone. Interestingly, these changes in sugar 'ornamentation' of the base steviol structure dramatically and unpredictably affect the properties of the individual steviol glycosides themselves. These traits include, without limitation, taste profile, crystallization point, solubility and perceived sweetness among other differences. Steviol glycosides with known structures include stevioside, rebaudioside A, rebaudioside B, rebaudioside C, rebaudioside D, rebaudioside E, rebaudioside F, rebaudioside M and dulcoside A. In terms of commercial use rebaudioside M has become generally regarded as safe (that is, it has 'GRAS' status) and is being studied for a wide range of uses in the food and beverage markets.

On a dry weight basis, stevioside, rebaudioside A, rebaudioside C, and dulcoside A, account for 9.1, 3.8, 0.6, and 0.30 percent of the total weight of the steviol glycosides found in wild type *Stevia* leaves, respectively, while the other steviol glycosides, such as Reb E are present in significantly lower amounts, with Reb D4 not being present at all. Extracts from *Stevia rebaudiana* plant are commercially available and in such extracts stevioside and rebaudioside A are most often the primary components. Comparatively, the other known steviol glycosides are typically present in the *stevia* extract as minor or trace components. For example, the amount of rebaudioside A in typical commercial preparations can vary from about 20% to more than 90% of the total steviol glycoside content, with the amount of rebaudioside B at about 1-2%, the amount of rebaudioside C about 7-15%, and the amount of rebaudioside D can be about 2% of the total steviol glycosides. In such extracts rebaudioside M is present only in vanishingly small amounts. Interestingly, Rebaudioside E is also one of the least abundant steviol glycosides present in *Stevia rebaudiana* plant varieties, accounting for less than 0.5% of total glycoside present.

As natural sweeteners, and as mentioned above, each of the different steviol glycosides have different degrees of sweetness, 'mouth feel' and specific after-tastes associated with them. Relative to table sugar (i.e., "sucrose") the sweetness of steviol glycosides is significantly higher. For example, stevioside is 100-150 times sweeter than sucrose but has a bitter after-taste as noted in numerous taste tests, while rebaudiosides A and E are 250-450 times sweeter than sucrose and the after-taste profile is much better than stevioside. However, these steviol glycosides themselves still retain a noticeable aftertaste. Accordingly, it is generally known that the taste profiles of *stevia* extracts are profoundly affected by the relative content of the various steviol glycosides in the extract, which in turn may be affected by the environmental conditions experienced by the underlying plants and the extraction process used. These variations in plant production, weather conditions and extraction conditions can lead to inconsistent compositions of the steviol glycosides in the *stevia* extracts, such that the taste profile varies strongly among different batches of extraction products. The taste profile of *stevia* extracts also can be affected by plant-derived or environment-derived contaminants (such as pigments, lipids, proteins, phenolics and saccharides) that remain in the product after the extractions process. These contaminants typically have their own off-flavors, making the resultant extract undesirable for use in consumer products. In addition, the cost of isolating individual or specific combinations of steviol rebaudiosides that are not abundant in *stevia* extracts is cost and resource prohibitive. Given that there is a limited quality and availability of some specific steviol glycosides, commercial supply can be better addressed by bio-conversion, where natural enzymes, or specific microbes can be modified to carry needed enzymes and use commercially significant fermentation processes to specifically increase the production of glycosides of interest. For example, bio-conversion of Stevioside to Reb E has been reported previously (see, Yu et al., U.S. application Ser. No. 15/016,589, published as US Patent Application Publication Number US2016/0207954) via a fermentation pathway with modified microbes. Alternatively, other non-biologic synthetic means can be used to develop steviol glycosides of interest.

Accordingly, there is a need for steviol glycosides with better and more consistent taste profiles to be developed as commercial products and for such steviol glycosides to utilize a relative common starting substrate, such as more abundant steviol glycosides as starting molecules, so that such production of desirable glycosides can be commercially as cost effective as possible.

SUMMARY OF THE INVENTION

The present disclosure encompasses a method of producing Reb D4 from Reb E, such as in a cellular system.

In particular, the current disclosure provides for the production of steviol glycoside rebaudioside D4 "Reb D4" which is identified as (13-[(2-O-β-D-glucopyranosyl-β-D- glucopyranosyl) oxy] ent-kaur-16-en-19-oic acid-[(2-O-β-D-glucopyranosyl-3-O-β-D-glucopyranosyl-β-D-glucopyranosyl) ester]) by a specific UDP-glycosyltransferase from Reb E.

The current methods provide an approach for the synthesis of specific steviol glycosides using a specific synthetic pathway.

In some aspects, the disclosure provides a mutant CP1 enzyme comprising the amino acid sequence of SEQ ID NO: 7. In some aspects, the disclosure provides a recombinant polypeptide comprising an amino acid sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 7. In some embodiments, the recombinant polypeptide has the same or substantially the same activity as a mutant CP1 enzyme as described herein, e.g., a mutant CP1 enzyme comprising the amino acid sequence of SEQ ID NO: 7.

In some aspects, the disclosure provides a nucleic acid comprising the nucleotide sequence of SEQ ID NO: 8. In some aspects, the disclosure provides a nucleic acid comprising a nucleotide sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 8. In some embodiments, the nucleotide sequence encodes a mutant CP1 enzyme as described herein, e.g., a mutant CP1 enzyme comprising the amino acid sequence of SEQ ID NO: 7.

In some aspects, the disclosure provides a mutant CP1 enzyme comprising the amino acid sequence of SEQ ID NO: 9. In some aspects, the disclosure provides a recombinant polypeptide comprising an amino acid sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 9. In some embodiments, the recombinant polypeptide has the same or substantially the same activity as a mutant CP1 enzyme as described herein, e.g., a mutant CP1 enzyme comprising the amino acid sequence of SEQ ID NO: 9.

In some aspects, the disclosure provides a nucleic acid comprising the nucleotide sequence of SEQ ID NO: 10. In some aspects, the disclosure provides a nucleic acid comprising a nucleotide sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 10. In some embodiments, the nucleotide sequence encodes a mutant CP1 enzyme as described herein, e.g., a mutant CP1 enzyme comprising the amino acid sequence of SEQ ID NO: 9.

In some aspects, the disclosure provides a mutant HV1 enzyme comprising the amino acid sequence of SEQ ID NO: 11. In some aspects, the disclosure provides a recombinant polypeptide comprising an amino acid sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 11. In some embodiments, the recombinant polypeptide has the same or substantially the same activity as a mutant HV1 enzyme as described herein, e.g., a mutant HV1 enzyme comprising the amino acid sequence of SEQ ID NO: 11.

In some aspects, the disclosure provides a nucleic acid comprising the nucleotide sequence of SEQ ID NO: 12. In some aspects, the disclosure provides a nucleic acid comprising a nucleotide sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 12. In some embodiments, the nucleotide sequence encodes a mutant HV1 enzyme as described herein, e.g., a mutant HV1 enzyme comprising the amino acid sequence of SEQ ID NO: 11.

In some aspects, the disclosure provides a host cell comprising a vector capable of producing a C1m2 enzyme having the amino acid sequence of SEQ ID NO: 7. In some aspects, the disclosure provides a host cell comprising a vector capable of producing a C1m3 enzyme having the amino acid sequence of SEQ ID NO: 9. In some aspects, the disclosure provides a host cell comprising a vector capable of producing a mutant HV1 enzyme having the amino acid sequence of SEQ ID NO: 11. In some embodiments, the host cell is selected from the group consisting of a bacteria, a yeast, a filamentous fungi, a cyanobacteria algae and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Escherichia; Klebsiella; Pantoea; Salmonella Corynebacterium; Clostridium*; and *Clostridium acetobutylicum*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (Oryza sativa); *Hordeum vulgare*; switchgrass (*Panicum vigratum*); *Brachypodium* spp.; *Brassica* spp.; and *Crambe abyssinica*.

In some aspects, the disclosure provides a method of producing a steviol glycoside composition, the method comprising incubating a substrate with a recombinant polypeptide comprising an amino acid sequence having at least 80% (e.g., at least 80%, at least 85%, at least 90%, at least 91%, at least 92%, at least 93%, at least 94%, at least 95%, at least 96%, at least 97%, at least 98%, at least 99%, or 100%) identity to SEQ ID NO: 7. In some embodiments, the recombinant polypeptide is a UDP-glycosyltransferase having at least 80% (e.g., at least 80%, at least 85%, at least 90%, at least 91%, at least 92%, at least 93%, at least 94%, at least 95%, at least 96%, at least 97%, at least 98%, at least 99%, or 100%) identity to SEQ ID NO: 7. In some embodiments, the substrate is selected from the group consisting of stevioside or rebaudioside E and combinations thereof. In some embodiments, the steviol glycoside compound produced by the method is rebaudioside D4 such that the steviol glycoside composition comprises rebaudioside D4.

In some aspects, the disclosure provides a method of producing rebaudioside D4, the method comprising incubating a substrate with a recombinant polypeptide comprising an amino acid sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 7. In some embodiments, the substrate is selected from the group consisting of Reb E, stevioside, and combinations thereof. In some embodiments, the method further comprises incubating a recombinant sucrose synthase with the substrate and the recombinant polypeptide.

In some aspects, the disclosure provides a method for synthesizing rebaudioside D4 from rebaudioside E, the method comprising (a) preparing a reaction mixture comprising rebaudioside E, a substrate selected from the group consisting of sucrose, uridine diphosphate (UDP) and uridine diphosphate glucose (UDP-glucose), and C1m2, and (b) incubating the reaction mixture for a sufficient time to produce rebaudioside D4, wherein a glucose is covalently coupled to the rebaudioside E to produce rebaudioside D4. In some embodiments, the method further comprises adding a sucrose synthase to the reaction mixture. In some embodiments, the sucrose synthase is selected from the group consisting of an *Arabidopsis* sucrose synthase 1, an *Arabidopsis* sucrose synthase 3 and a *Vigna radiate* sucrose synthase. In some embodiments, the sucrose synthase is an *Arabidopsis thaliana* sucrose synthase 1. In some embodiments, the Reb D4 produced is greater than 70% (e.g., greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, greater than 99%, or 100%) pure. In some embodiments, the method further comprises adding a HV1 enzyme to the reaction mixture.

In some aspects, the disclosure provides a method for synthesizing rebaudioside D4 from rebaudioside E, the method comprising (a) preparing a reaction mixture comprising rebaudioside E, a substrate selected from the group consisting of sucrose, uridine diphosphate (UDP) and uridine diphosphate glucose (UDP-glucose), and C1m3, and (b) incubating the reaction mixture for a sufficient time to produce rebaudioside D4, wherein a glucose is covalently coupled to the rebaudioside E to produce rebaudioside D4. In some embodiments, the method further comprises adding a sucrose synthase to the reaction mixture. In some embodiments, the sucrose synthase is selected from the group consisting of an *Arabidopsis* sucrose synthase 1, an *Arabidopsis* sucrose synthase 3 and a *Vigna radiate* sucrose synthase. In some embodiments, the sucrose synthase is an *Arabidopsis thaliana* sucrose synthase 1. In some embodiments, the Reb D4 produced is greater than 70% (e.g., greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, greater than 99%, or 100%) pure. In some embodiments, the method further comprises adding a HV1 enzyme to the reaction mixture.

In some aspects, the disclosure provides a sweetener comprising a steviol glycoside composition or steviol glycoside produced by a method as described above or as otherwise described herein.

In some aspects, the disclosure provides a GXT6 enzyme comprising the amino acid sequence of SEQ ID NO: 5. In some aspects, the disclosure provides a recombinant polypeptide comprising an amino acid sequence having at least 90% (e.g., at least 90%, at least 91%, at least 92%, at least 93%, at least 94%, at least 95%, at least 96%, at least 97%, at least 98%, at least 99%, or 100%) identity to SEQ ID NO: 5. In some embodiments, the recombinant polypeptide has the same or substantially the same activity as a GXT6 enzyme as described herein, e.g., a GXT6 enzyme comprising the amino acid sequence of SEQ ID NO: 5. In some aspects, the disclosure provides a host cell comprising a vector capable of producing a GXT6 enzyme having the amino acid sequence of SEQ ID NO: 5.

In some aspects, the disclosure provides a nucleic acid comprising the nucleotide sequence of SEQ ID NO: 6.

In some aspects, the disclosure provides a CP1 enzyme comprising SEQ ID NO: 3. In some aspects, the disclosure provides a nucleic acid comprising the nucleotide sequence of SEQ ID NO: 4.

In some aspects, the disclosure provides a method of producing Reb M using the enzymes and substrates described in FIG. 9, or a subset thereof (e.g., starting with Stevioside, Reb E, or Reb D4 and/or utilizing HV1, C1m2, C1m3, UGT76G1, CP1 and/or CR1). In some embodiments, the Reb M is produced using an in vitro reaction mixture containing the enzymes and substrates described in FIG. 9, or a subset thereof (e.g., starting with Stevioside, Reb E, or Reb D4 and/or utilizing HV1, C1m2, C1m3, UGT76G1, CP1 and/or CR1). In some embodiments, the Reb M is produced in vivo in a cell that expresses the enzymes described in FIG. 9, or a subset thereof (e.g., HV1, C1m2, C1m3, UGT76G1, CP1 and/or CR1), wherein the cell is incubated with a substrate described in FIG. 14 (e.g., Stevioside, Reb E, or Reb D4). In some embodiments, the cell is a yeast cell. In some embodiments, the cell is a bacterial cell. In some embodiments, the cell is a plant cell.

In terms of product/commercial utility there are several dozen products containing steviol glycosides on the market in the United States and can be used in everything from analgesics to pest repellents as well as in foods and as a dietary supplement. Products containing steviol glycosides can be aerosols, liquids, gels or granular formulations.

As for the cellular system, in some embodiments, it is selected from the group consisting of bacteria, yeast, and a combination thereof, or any cellular system that would allow the genetic transformation with the selected genes and thereafter the biosynthetic production of the desired steviol glycosides from steviol. In a most preferred microbial system, *E. coli* are used to produce the desired steviol glycoside compounds.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DETAILED DESCRIPTION OF THE INVENTION

Figure 1:
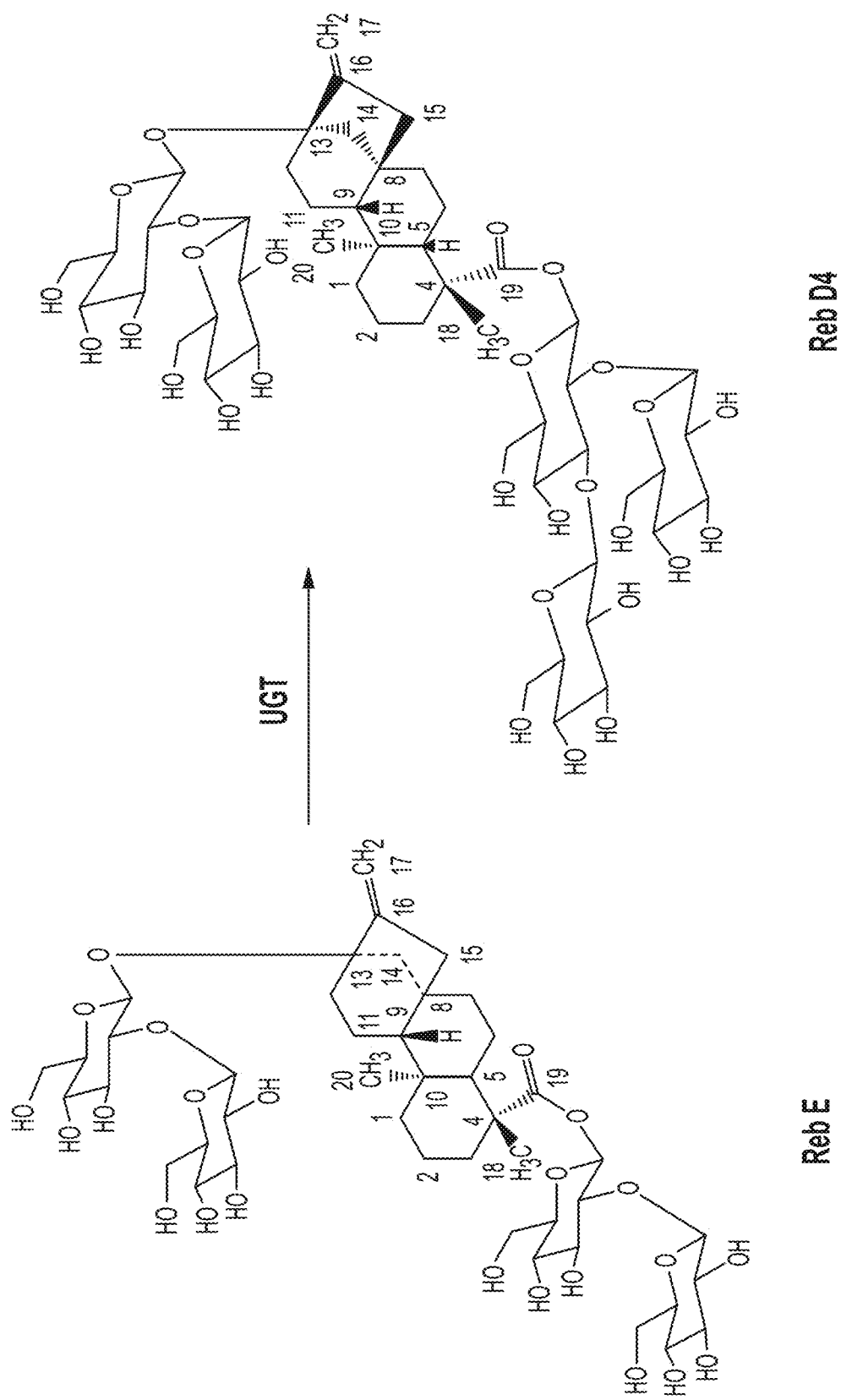
FIG. 1. Shows a Steviol glycoside Biosynthetic Pathway of the production of Reb D4 from Reb E.

Explanation of Terms Used Herein:

Steviol Glycosides are a class of chemical compounds responsible for the sweet taste of the leaves of the South American plant Stevia rebaudiana (Asteraceae), and can be used as sweeteners in food, feed and beverages.

Definitions:

Cellular system is any cells that provide for the expression of ectopic proteins. It includes bacteria, yeast, plant cells and animal cells. It includes both prokaryotic and eukaryotic cells. It also includes the in vitro expression of proteins based on cellular components, such as ribosomes.

Coding sequence is to be given its ordinary and customary meaning to a person of ordinary skill in the art, and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current disclosure, a yeast is a eukaryotic, single-celled microorganism classified as a member of the fungus kingdom. Yeasts are unicellular organisms which evolved from multicellular ancestors but with some species useful for the current disclosure being those that have the ability to develop multicellular characteristics by forming strings of connected budding cells known as pseudohyphae or false hyphae.

The names of the UGT enzymes used in the present disclosure are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

Structural Terms:

As used herein, the singular forms "a, an" and "the" include plural references unless the content clearly dictates otherwise.

To the extent that the term "include," "have," or the like is used in e description or the claims, such term is intended to be inclusive in a manner similar to the term "comprise" as "comprise" is interpreted when employed as a transitional word in a claim.

The word "exemplary" is used herein to mean "serving as an example, instance, or illustration". Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxy inosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference, peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it can affect the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the craft, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "transformed".

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The present disclosure relates, in part, to the use of Reb E in the production of Reb D4. From a biological perspective, all steviol glycosides are formed by a series of glycosylation reactions of steviol, which typically are catalyzed by UDP-glycosyltransferase (UGT) enzymes using uridine 5'-diphosphoglucose (UDP-glucose) as a donor of the sugar moiety. In plants, UGTs are a very divergent group of enzymes that can transfer a glucose residue from UDP-glucose to steviol. In these reactions stevioside is often an intermediate in the biosynthesis of various rebaudioside compounds. For example, glycosylation of stevioside at the C-3' at the C-13-O-glucose of stevioside yields rebaudioside A; while glycosylation at the C-2' at the 19-0-glucose position of stevioside yields rebaudioside E.

According to the current disclosure, the specific and directed glycosylation of rebaudioside E (at the C-19-O-glucose) can produce rebaudioside Reb D4 from Reb E which can then be further directed towards the glycosylation of Reb D4 by UGT enzymes to produce rebaudioside M. The synthetic steps to produce Reb D4 from Reb E enzymatically have not been previously reported. The first committed step of steviol glycoside biosynthesis pathway involves conversion of ent-kaurenoic acid to steviol by the activity of enzyme KAH. It has been shown that UGT76G1 exhibits multiple glycosylation activities towards steviol bioside forming rebaudioside B, and stevioside resulting in the production of rebaudioside A. In addition, the interaction affinity of KAH, UGT85C2, UGT74G1 and UGT76G1 has been evaluated for ent-kaurenoic acid and steviol. The model predicted for KAH showed highest affinity for the ligand steviol, followed by steviol-monoside and ent-kaurenoic acid. The docking results for the three-dimensional model of UGT76G1 suggested its highest binding affinity for ent-kaurenoic acid but also suggest that these enzymes have the ability to interact with more than one of the ligands in the steviol glycoside biosynthesis pathway. According to the current disclosure, mutations in the domains in UGT76G1 can cause specific alteration of glycosylation activity leading to the production of alternate rebaudiosides.

According to the current disclosure, a practical approach to improve the taste quality of *stevia* extracts is to increase the yield of those rebaudioside compounds that have more desirable taste characteristics in general and to do this via a more productive synthetic pathway. Of those steviol glycosides tested many believe that Reb M has the most desirable taste and chemical characteristics for use in a variety of food and beverages. As stated above, however, the plant has vanishingly small amounts of this compound present in its leaves and therefore an alternative biosynthetic process needs to be developed to enable the large-scale production of this glycoside as well as to provide alternate sweeteners to the food and beverage industry. Part of this pathway is provided herein.

Accordingly, there is a need for steviol glycosides with better and more consistent taste profiles to be developed as commercial products and for such steviol glycosides to utilize a relative common starting substrate, such as more abundant steviol glycosides as starting molecules, so that such production of desirable glycosides can be commercially as cost effective as possible. The present disclosure provides a method of producing rebaudioside D4 from stevioside through rebaudioside E.

Going further, the extraction process from plants, typically employs solid-liquid extraction techniques using solvents like hexane, chloroform, and ethanol for steviol glycoside recovery (Catchpole et al., 2003). However, solvent extraction is itself energy intensive, leads to problems of toxic waste disposal, requires extensive acreage for the plants themselves to be grown and yields a product that requires further purification for minor constituents to be recovered. Thus, new production methods are also needed to reduce costs of steviol glycoside production and lessen the environmental impact of large scale cultivation and processing (Yao et al., 1994). One such potential solution is the use of fermentation bio-conversion technology that allows the production in certain microbial species that increases the selectivity, abundance and purity of desired steviol glycosides available for commerce.

In addition to the above, while consumers approve and actively seek natural and biological sources for food, feed, flavor or medicinal components they are also concerned about sourcing, consistent taste profile and environmentally sustainable production. Into this situation, the microbial fermentation and production methods of the current disclosure provide Reb D4 in quantities useful for a variety of industries and research while doing so in a more natural fashion than inorganic synthesis or current plant extraction techniques.

Accordingly, a need exists for the development of a novel method of producing Reb D4 economically and conveniently to further enable human and animal consumption. Specifically, the current disclosure provides methods to use Reb E to produce Reb D4 via engineered microorganisms.

The present disclosure relates to the production of a steviol glycoside of interest, Reb D4 from Reb E using UGT enzymes to allow that conversion. The subject technology provides recombinant polypeptides with UDP glycosyltransferase activities, such as 1,3-19-O-glucose glycosylation activity and 1,3-13-O-glucose glycosylation activity for synthesizing steviol glycosides. The recombinant polypeptide of the subject technology is useful for the biosynthesis of steviol glycoside compounds. In the present disclosure, UDP-glycosyltransferase (UGT) refers to an enzyme that transfers a sugar residue from an activated donor molecule (typically UDP-glucose) to an acceptor molecule. The 1,3-19-O-glucose glycosylation activity refers to an enzymatic activity that transfers a sugar moiety to the C-3' of the 19-O glucose moiety of rebaudioside E to produce rebaudioside D4 (Reb D4) (FIG. 1).

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N. Y., 1989 (hereinafter "Maniatis"); and by Silhavy. T. J., Bennan, M. L. and Enquist, L. W. EXPERIMENTS WITH GENE FUSIONS; Cold Spring Harbor Laboratory: Cold Spring Harbor, N. Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family 1 GT enzymes, also known as the UDP glycosyltransferases (UGTs), transfer UDP-activated sugar moieties to specific acceptor molecules. These are the molecules that transfer such sugar moieties in the steviol glycosides to create various rebaudiosides. Each of these UGTs have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

Several molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt ended DNA segments. The blunt-ended segments are then incubated with a large molar excess of linker molecules in the presence of an enzyme that can catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell expression systems and expression vectors containing regulatory sequences that direct high level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (ss) of the ribulose-1, 5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll alb binding protein. These two promoters are known to be light-induced in plant cells (see, for example, GENETIC ENGINEERING OF PLANTS, AN AGRICULTURAL PERSPECTIVE, A. Cashmore, Plenum, N. Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Precursor Synthesis to Reb E

As previously stated steviol glycosides are the chemical compounds responsible for the sweet taste of the leaves of the South American plant *Stevia rebaudiana* (*Asteraceae*) and in the plant *Rubus chingii* (*Rosaceae*). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current disclosure is to take common or inexpensive precursors such as steviol or rubososide derived chemically or produced via biosynthesis in engineered microbes such as bacteria and/or yeast and to synthesize targeted steviol glycosides through known or inexpensive methods, such as Reb E.

Aspects of the present disclosure relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. This should occur in a microbial strain that expresses an endogenous isoprenoid synthesis pathway, such as the non-mevalonate (MEP) pathway or the mevalonic acid pathway (MVA). In some embodiments, the cell is a bacterial cell, including *E. coli*, or yeast cell such as a *Saccharomyces* cell, *Pichia* cell, or a *Yarrowia* cell. In some embodiments, the cell is an algal cell or a plant cell.

Thereafter, the precursor is recovered from the fermentation culture for use in chemical synthesis. Typically, this is steviol though it can be kaurene, or a steviol glycoside from the cell culture. In some embodiments, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside D, rebaudioside E, rebaudioside F or dulcoside A. In some embodiments, the terpenoid produced is steviobioside or stevioside. It should also be appreciated that in some embodiments, at least one enzymatic step, such as one or more glycosylation steps, are performed ex vivo.

Part of the disclosure is the production of the Reb E steviol glycoside that is then subject to further enzymatic conversion to Reb D4. According to the current disclosure, the biosynthesis for the conversion of microbially produced steviol to a desired steviol glycoside (here Reb D4) occurs when the diterpenoid steviol is converted from rubusoside and stevioside using multi-step chemical assembly of sugar moieties into the steviol backbone.

Biosynthesis of Steviol Glycosides

As described herein, the recombinant polypeptides of the present technology have UDP-glycosyltransferase activities and are useful for developing biosynthetic methods for preparing steviol glycosides that are either not present in nature or typically of low abundance in natural sources, such as rebaudioside D4 and rebaudioside M, respectively. The recombinant polypeptides of the present technology have UDP-glycosyltransferase activities, are useful for developing biosynthetic methods for preparing novel steviol glycosides, such as rebaudioside D4 and reaching the synthetic production of rebaudioside M.

The substrate can be any natural or synthetic compound capable of being converted into a steviol glycoside compound in a reaction catalyzed by one or more UDP glycosyltransferases. For example, the substrate can be natural *stevia* extract, steviol, steviol-13-O-glucoside, steviol-19-O-glucoside, steviol-1, 2-bioside, rubusoside, stevioside, rebaudioside A, rebaudioside G or rebaudioside E. The substrate can be a pure compound or a mixture of different compounds. Preferably, the substrate includes a compound selected from the group consisting of rubusoside, stevioside, steviol, rebaudioside A, rebaudioside F and combinations thereof.

Methods described herein also provide a coupling reaction system in which the recombinant peptides described herein can function in combination with one or more additional enzymes to improve the efficiency or modify the outcome of the overall biosynthesis of steviol glycoside compounds. For example, the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction. In some embodiments, the enzyme is a sucrose synthase. In some embodiments, the additional enzyme is *Arabidopsis* sucrose synthase 1, an *Arabidopsis* sucrose synthase 3 or a *Vigna radiate* sucrose synthase. Such enzymes are disclosed, e.g., in U.S. Pat. No. 9,522,929, which is incorporated herein by reference.

In another embodiment, methods of the subject technology further include incubating a recombinant UDP-glycosyltransferase with the recombinant sucrose synthase, the substrate, and the recombinant polypeptide described herein. The recombinant UDP-glycosyltransferase can catalyze a different glycosylation reaction than the one catalyzed by the recombinant polypeptide of the subject technology.

Suitable UDP-glycosyltransferase includes any UGT known in the art or described herein as capable of catalyzing one or more reactions in the biosynthesis of steviol glycoside compounds, such as UGT85C2, UGT74G1, UGT76G1, or the functional homologs thereof.

Typically, in an in vitro method of the subject technology, UDP-Glucose is included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM.

Typically, in an in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

Typically, the reaction temperature of the in vitro method is from about 20° C. to about 40° C., suitably from 25° C. to about 37° C., more suitably from 28° C. to about 32° C.

One with skill in the art will recognize that the steviol glycoside composition produced by the methods described herein can be further purified and mixed with other steviol glycosides, flavors, or sweeteners to obtain a desired flavor or sweetener composition. For example, a composition enriched with rebaudioside M or Reb D4 produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D4) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside D4, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

One with skill in the art will recognize that the steviol glycoside composition produced by the methods described herein can be further purified and mixed with other steviol glycosides, flavors, or sweeteners to obtain a desired flavor or sweetener composition. For example, a composition enriched with rebaudioside D4 produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D4) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside D4, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, PASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment. Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL: 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the C1m2 and C1m3 sequences of the current disclosure are capable of directing the production of a variety of steviol glycosides and have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

EXAMPLES

1. Enzymatic Synthesis of Reb D4

There are several enzymatic methods of making Reb D4. One method starting from Reb E is presented here.

The expression construct was transformed into E. coli BL21 (DE3), which was subsequently grown in LB media containing 50 µg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000× g; 10 min; 4° C.). The cell pellets were collected and were either used immediately or stored at −80° C.

The cell pellets were re-suspended in lysis buffer (50 mM potassium phosphate buffer, pH 7.2, 25 µg/ml lysozyme, 5 µg/ml DNase I, 20 mM imidazole, 500 mM NaCl, 10% glycerol, and 0.4% TRITON X-100). The cells were disrupted by sonication at 4° C., and the cell debris was clarified by centrifugation (18,000× g; 30 min). The supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged B-glu1 recombinant polypeptide was eluted by equilibration buffer containing 250 mM imidazole.

HPLC analysis was performed using a Dionex ultimate 3000 system (Sunnyvale, Calif.), including a quaternary pump, a temperature controlled column compartment, an auto sampler and a UV absorbance detector. Synergi Hydro-RP column with guard column was used for the characterization of steviol glycosides. Acetonitrile in water was used for elution in HPLC analysis. The detection wavelength was 210 nm.

Mutant Enzymes

Based on UGT76G1 structure, a series of circular permutations (PLoS computational Biology, 2012; BIOINFORMATICS, 2015) and a set of mutations were designed and their function was tested. Circular permutation analysis is a powerful tool to develop or modify enzymes of interest. After test several versions of circular permutations, significant activity was found in one version of UGT76G1. This circular mutation "circular permutation 1" ("CP1") has demonstrated significant activity in terms of glucosylation of the steviol core. According to the current disclosure, the activity of CP1 enzyme was studied and its ability to assist in the conversion of Reb D4 to Reb M was assessed. Broadly speaking, CP1 is a variant of UGT76G1 with its domains switched and identified mutation sites.

Based on the CP1 modeling analysis, multiple mutation sites for the CP1 enzyme were selected to test bioconversion of Reb E to Reb D4. After a series of such mutations, a handful of mutants were isolated that could function as desired with regard to glycosylation activity and ornamentation of the steviol core. The positional mutants away from the wild type CP1 are provided in Table 1. With these enzymes in hand, a genetically modified microbe was developed capable of bio-converting Reb E to rebaudioside D4 directly. For example, two CP1mutants (C1m2 and C1m3) were found that have high enzymatic activity for the bio-conversion of Reb E to Reb D4. C (SEQ ID NO: 7) includes two mutation sites and C1m3 (SEQ ID NO: 9) contains three mutation sites from the CP1 sequence.

TABLE 1

Mutation Sites of CP1.

| Position | Amino acid |
| --- | --- |
| 3 | W-L |
| 6 | L-A, L-G |
| 90 | T-A; T-G |
| 91 | S-G; S-L |
| 93 | V-A; V-G |
| 181 | S-G |
| 183 | F-V; F-A; F-G |
| 184 | G-A |
| 185 | L-A |
| 350 | G-A |
| 389 | L-V |
| 410 | S-G |
| 418 | H-V |
| 450 | T-A; T-G |
| 451 | K-A |
| 452 | D-A |
| 454 | K-L; K-V |

2. Identification the UGT Mutants with Activity for Reb D4 Production from Reb E:

To confirm the conversion of Reb E to rebaudioside D4 in vitro, the C1m2 and C1m3 enzyme mutants were assayed using Reb E as the steviol glycoside substrate. The recombinant polypeptide (10 μg) was tested in a 200 μL in vitro reaction system. The reaction system contained 50 mM potassium phosphate buffer, pH 7.2, 3 mM $MgCl_2$, 1 mg/ml Reb E substrate, and 1 mM UDP-glucose. The reaction was performed at 37° C. and terminated by adding 200 μL of 1-butanol. The samples were extracted three times with 200 μL of 1-butanol. The pooled fraction was dried and dissolved in 70 μL of 80% methanol for high-performance liquid chromatography (HPLC) analysis.

HPLC analysis was performed using a Dionex UPLC ultimate 3000 system (Sunnyvale, Calif.), including a quaternary pump, a temperature controlled column compartment, an auto sampler and a UV absorbance detector. Synergi Hydro-RP column with guard column was used for the characterization of steviol glycosides. Acetonitrile in water was used for elution in HPLC analysis. The detection wavelength was 210 nm. Reb D and Reb D4 has different retention time in the HPLC profile. However, Reb D4 and Reb E has close retention time. (FIGS. 2, A and B).

Figure 2:
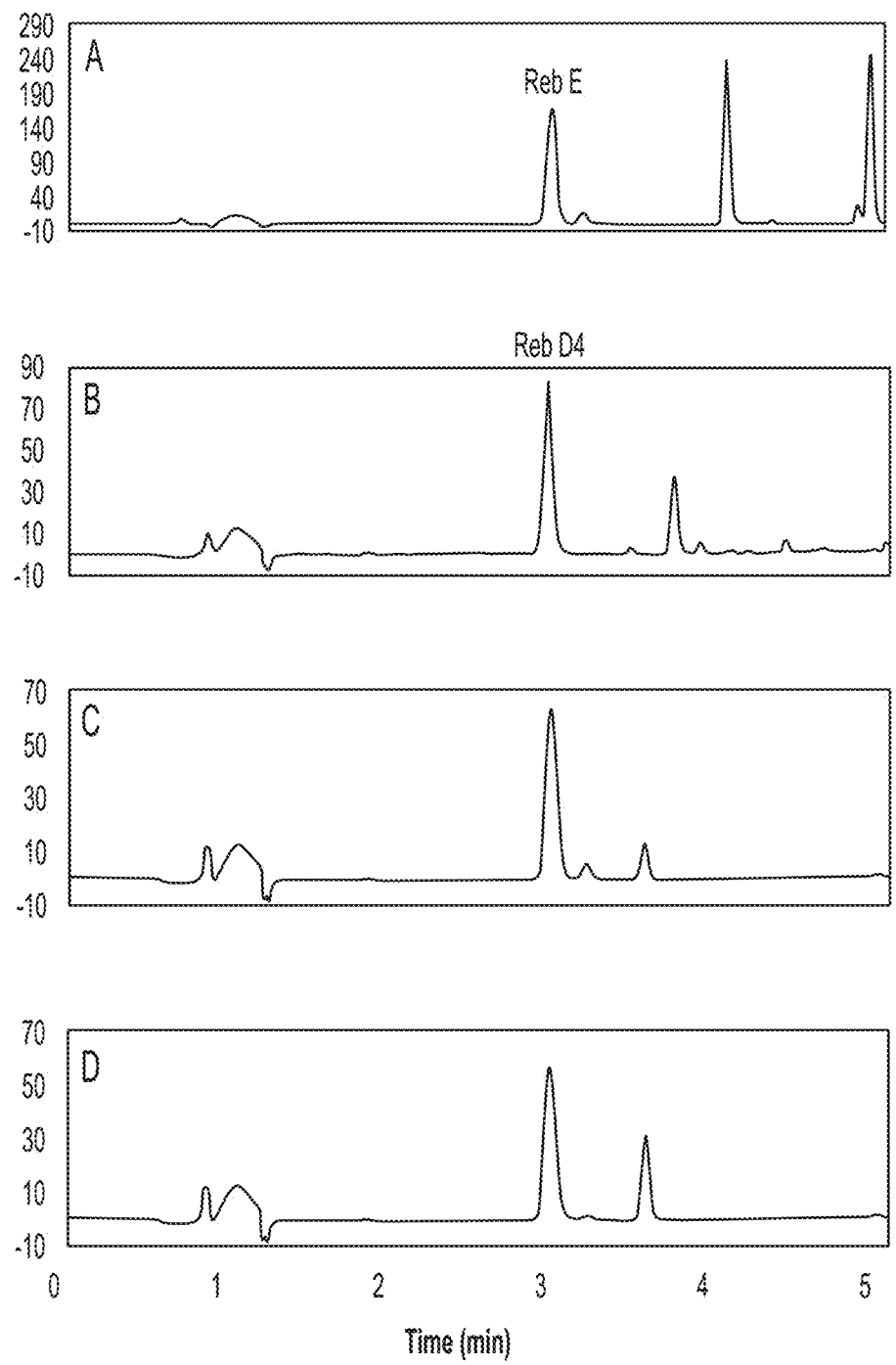
FIG. 2. Shows In vitro production of Reb D4 from Reb E catalyzed by C1m2 and C1m3 enzyme. A: shows the standard of rebaudioside E ("Reb E"). B: shows the standards of rebaudioside D4 ("Reb D4"). Reb D4 enzymatically produced by C1m2 (C) and C1m3 (D) at 16 hr.

As shown in FIG. 2, C1m2 and C1m3 enzyme can convert Reb E to a compound with similar retention time as Reb D4 standard, indicating these two mutants have the enzymatic activity for Reb D4 production.

3. Identification of Reb D4 Production by LC-MS Analysis

As shown in FIG. 2, the retention time of Reb E and Reb D4 is very close. It is difficult to distinguish Reb E and Reb D4 in the reactions by current HPLC methods. To confirm the conversion of Reb E to Reb D4, the produced compound was analyzed by LC-MS analysis.

In order to identify Reb D4 compound in the related reactions, samples from C1m2 and C1m3 bioconversion were analyzed by LC-MS using the Synergy Hydro-RP column. Mobile phase A was 0.1% formic acid in water, and mobile phase B was 0.1% formic acid in acetonitrile. The flow rate was 0.5 ml/minute. Mobile phase B was started at 20% B and maintained for 2 minutes. Then a linear gradient to 45% B over 15 minutes was run. Then % B was increased to 90% over 0.5 minutes and maintained for the following 8 minutes. The starting conditions were re-established over 0.5 minute and maintained for another 4.5 minutes prior to the next injection for re-equilibration of the column. Mass spectrometry analysis of the samples was done on the Bruker Impact II with an optimized method in positive ion mode. Funnel 1 RF was kept at 400Vp-p, Funnel 2 RF at 400 Vp-p, Transfer time of 120 μs and pre-pulse storage of 15 μs. A full calibration of the m/z scale was done with sodium formate clusters at the end of each run. All eluent was diverted to waste for the first 2 minutes using a secondary/optional 6-port valve to keep the source clean.

Figure 3:
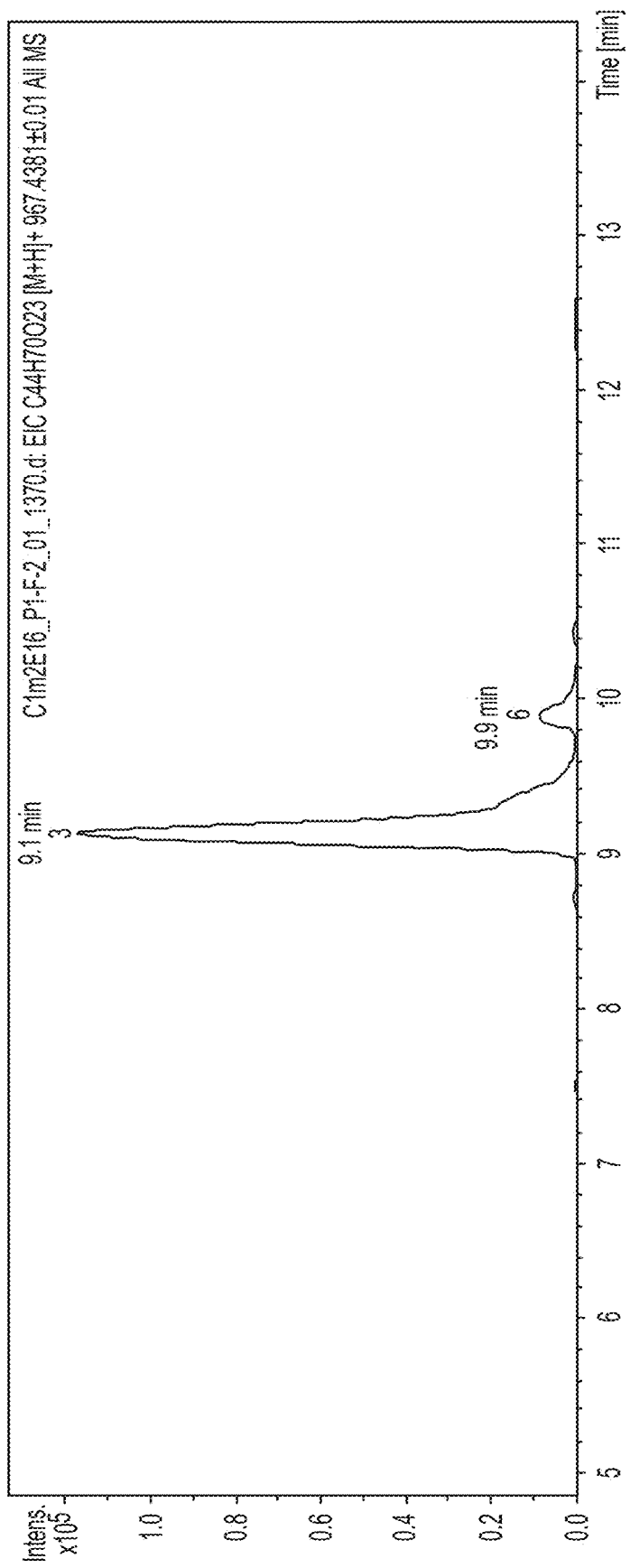
FIG. 3. Shows the LC-MS Analysis of the produced compound by C1m2 mutant.
Figure 3:
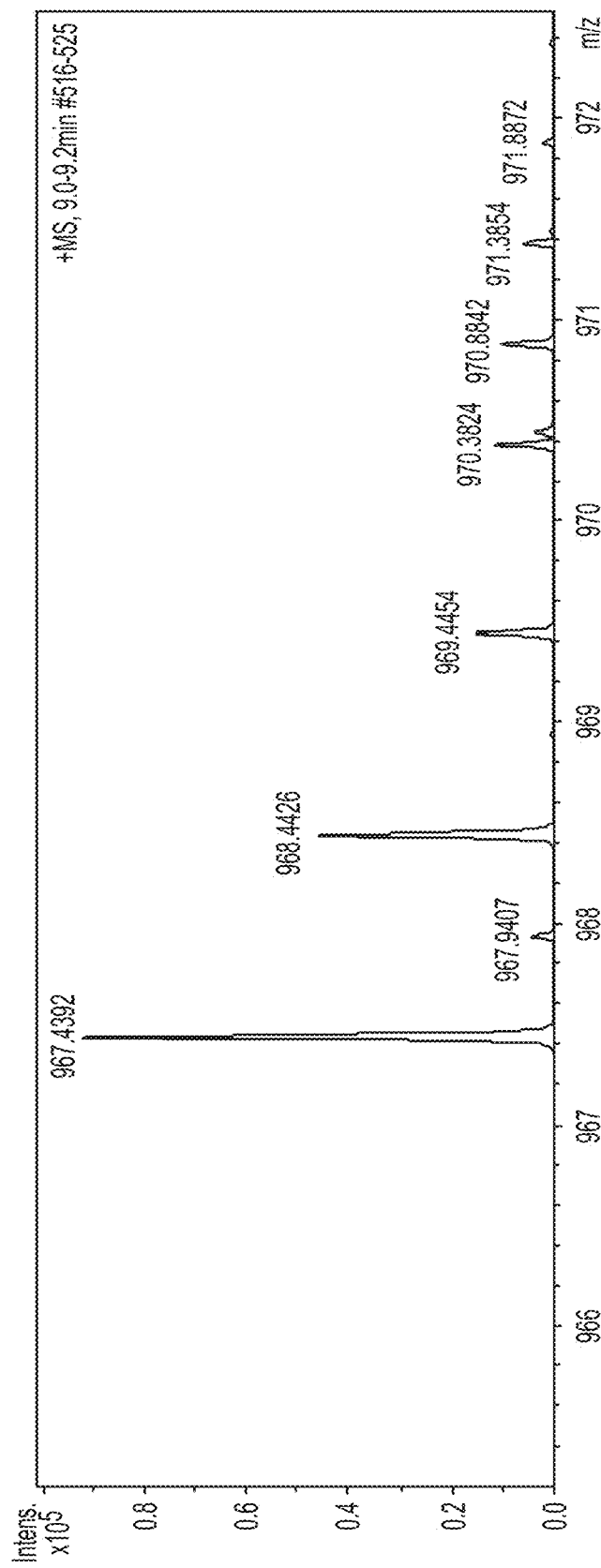
Figure 3:
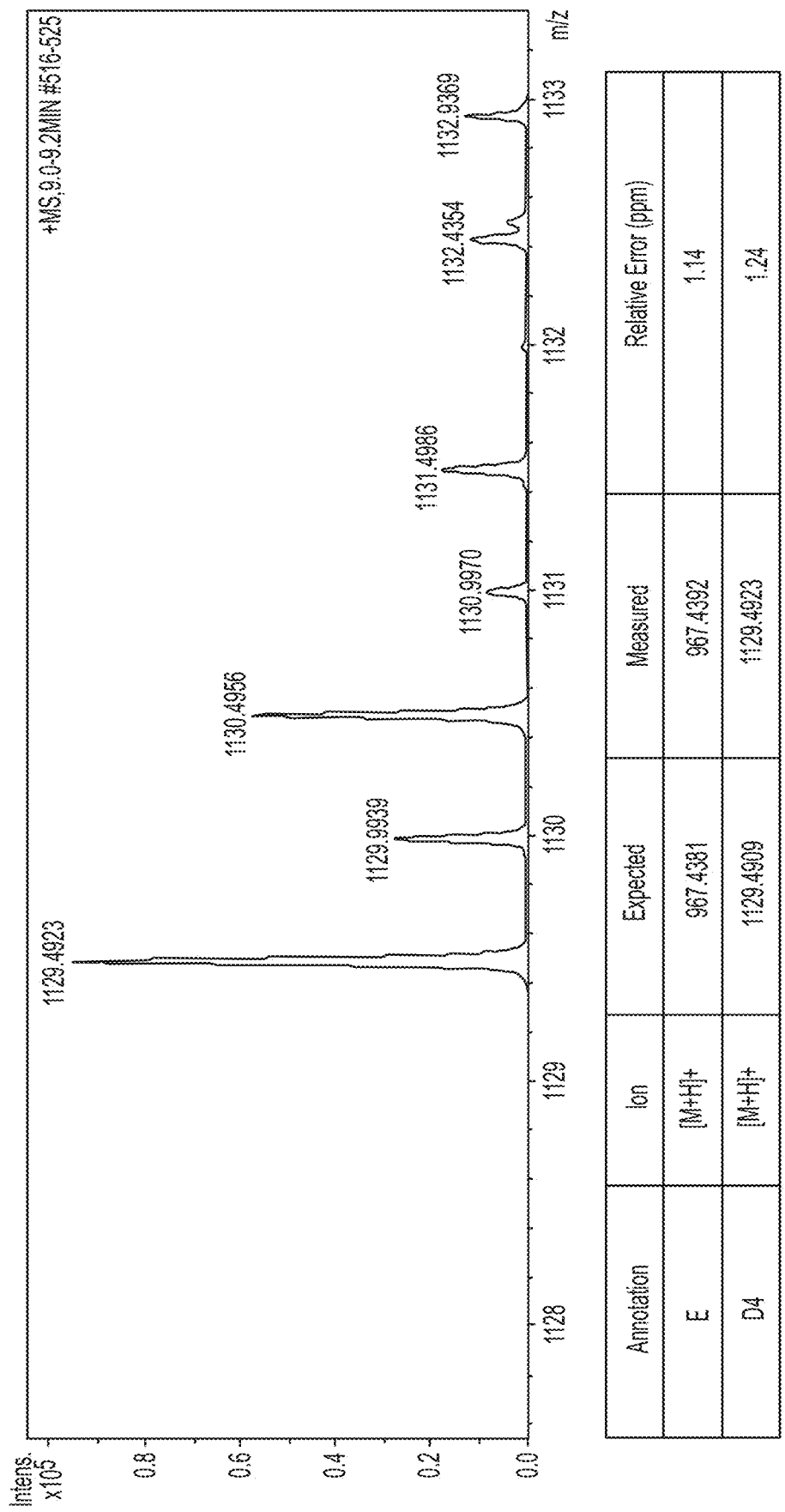
Figure 4:
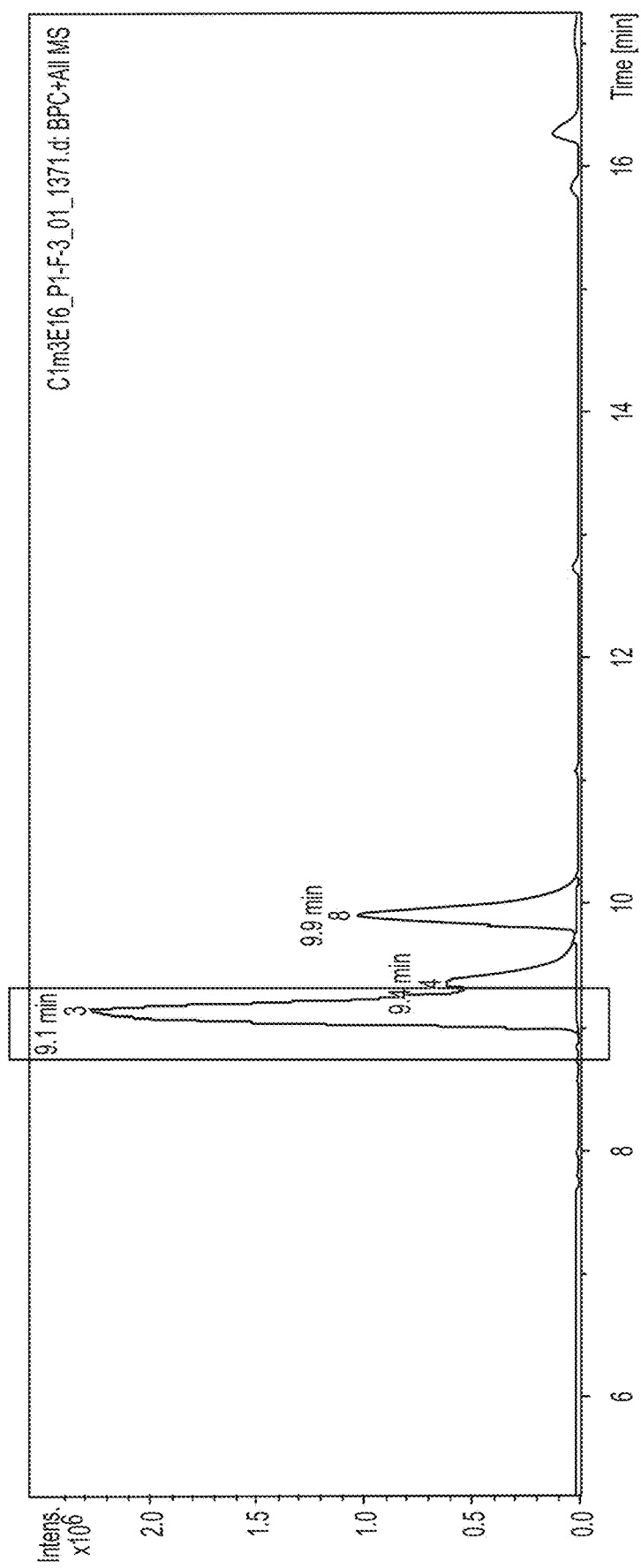
FIG. 4. Shows the LC-MS Analysis of the produced compound by C1m3 mutant.
Figure 4:
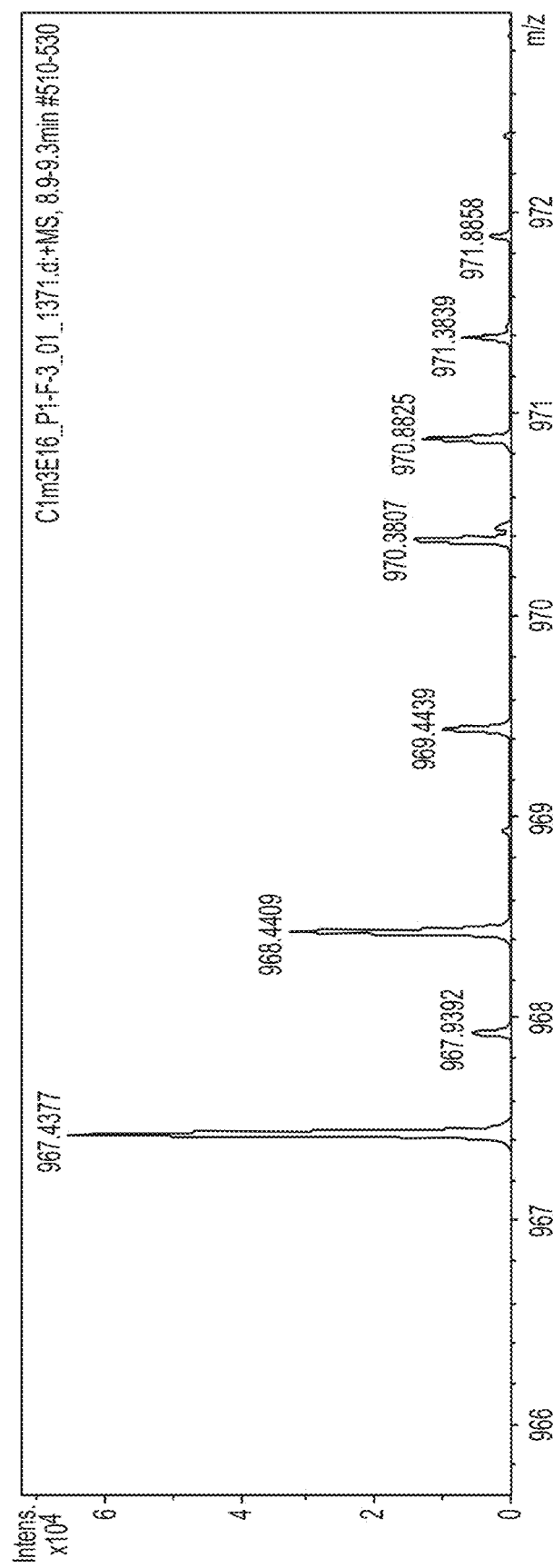
Figure 4:
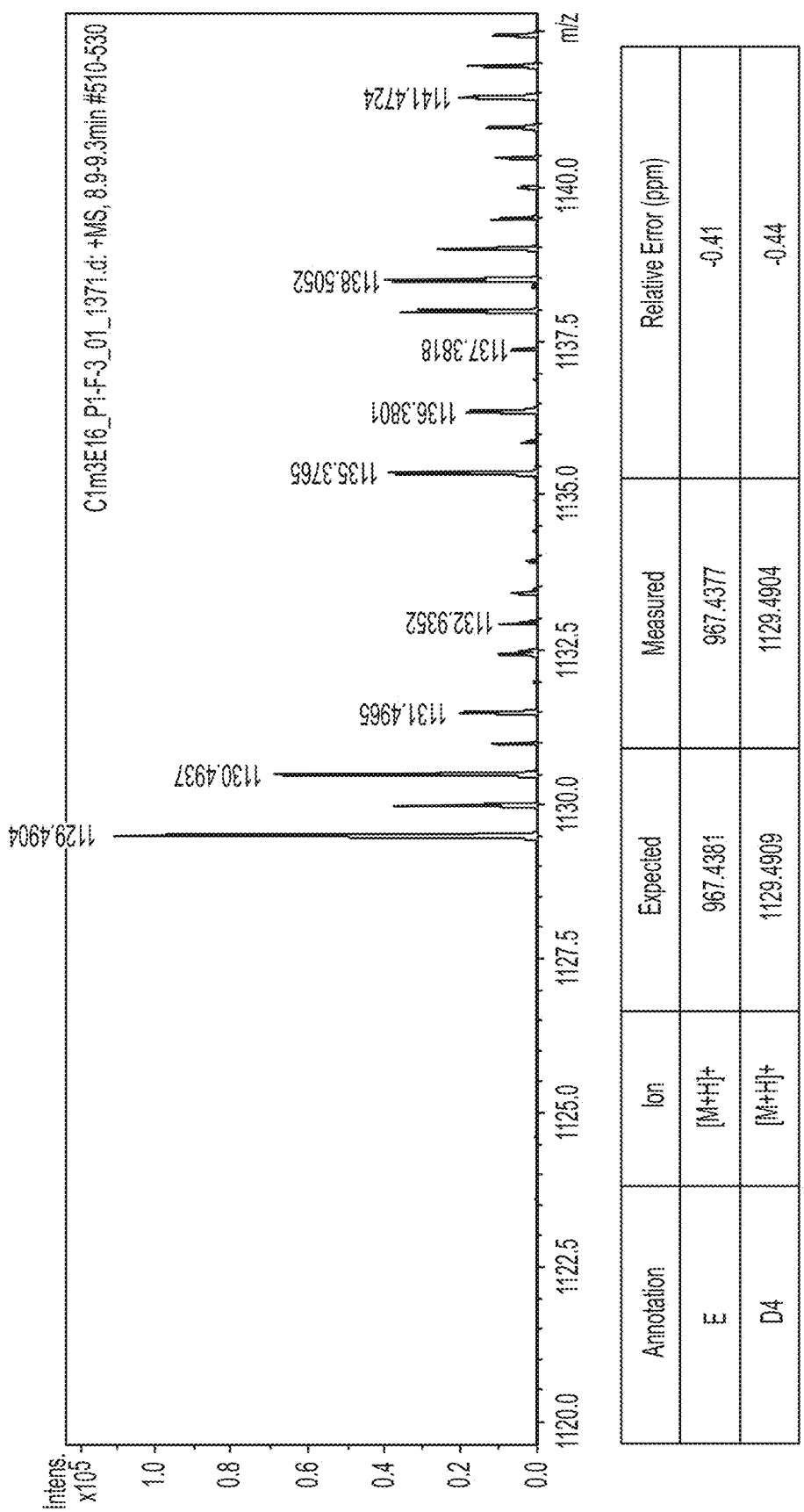

As shown in FIGS. 3 and 4, the produced compound has same molecular weight as Reb D4. Reb E substrate also can be detected at the same retention time. These results provide the evidence supporting Reb D4 production in these reactions was catalyzed by C1m2 or C1m3 enzyme.

4. Identification of Reb D4 Production by Enzymatic Assay

According to the current disclosure, an enzymatic assay was established to confirm the production of Reb D4. A beta-glucosidase assay was modified to detect Reb D4 production in the related reactions. In this assay beta-glucosidase can hydrolyze steviol glycosides to remove the glucose group(s). After screening, a beta-glucosidase (GXT6, SEQ: 5) was found that has the specific enzymatic activity to hydrolyze Reb D4, Reb E and Reb D. So, the enzymatic assay was generated to distinguish the three compounds present in the reactions of the current disclosure.

Figure 5:
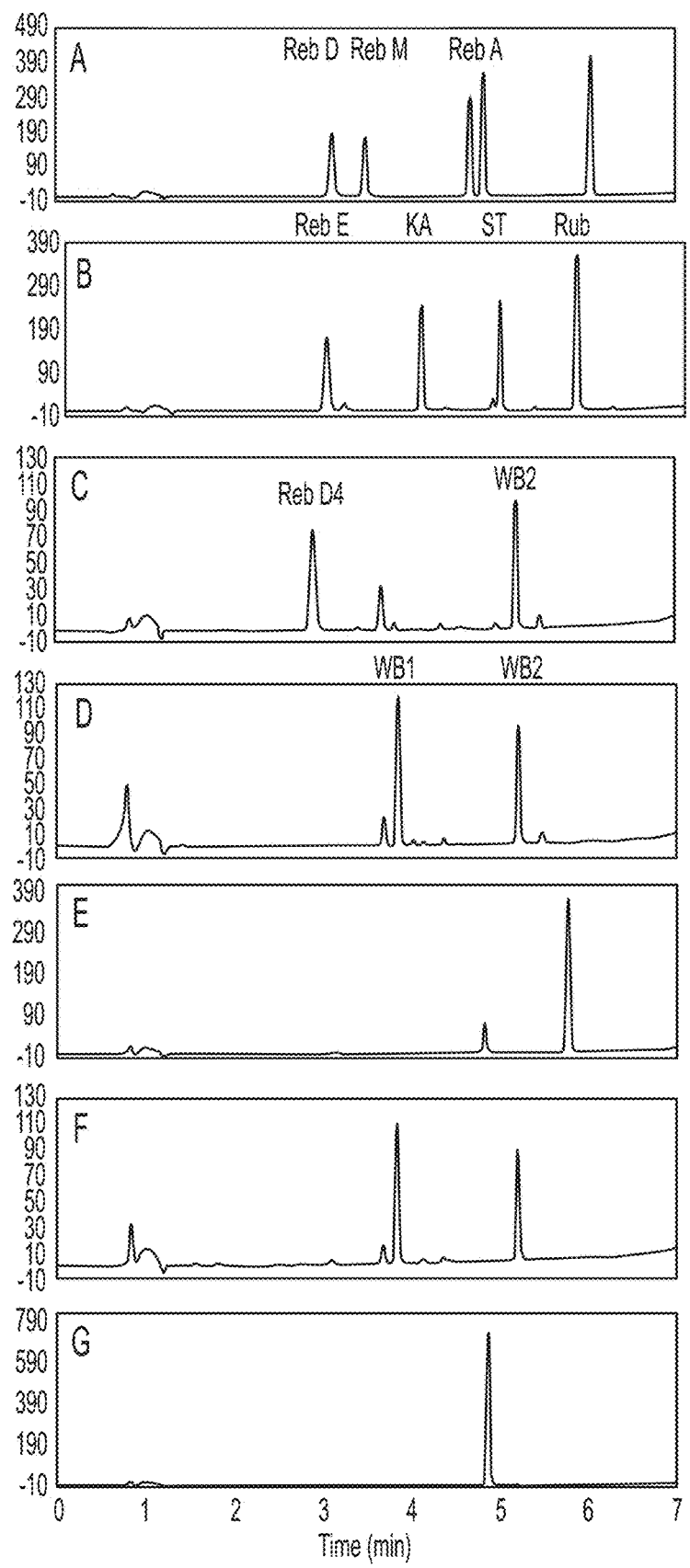
FIG. 5. Shows the Hydrolysis of Reb D4, Reb E and Reb D by GXT6 beta-glucosidase. Hydrolysis of Reb D4, Reb E and Reb D by GXT6 beta-glucosidase at 16 hr. A: shows the standards of rebaudioside D ("Reb D"), rebaudioside M ("Reb M") and rebaudioside A ("Reb A"). B: shows the standards of rebaudioside E ("Reb E"), rebaudioside KA("KA"), Stevioside ("ST") and rubusoside ("Rub"). C: shows the standard of rebaudioside D4 ("Reb D4") and Reb WB2 ("WB2") D: shows the standards of rebaudioside WB1 ("WB1") and Reb WB2 ("WB2"). E: shows hydrolysis of Reb E. F: hydrolysis of D4. G: shows hydrolysis of Reb D.

As shown in FIG. 5, GXT6 can hydrolyze Reb D4 to Reb WB1. Reb E can be hydrolyzed to stevioside and rubusoside by GXT6; Reb D can be hydrolyzed to Reb A by GXT6. All compounds have different retention times in the HPLC profile and can be distinguished clearly.

Figure 6:
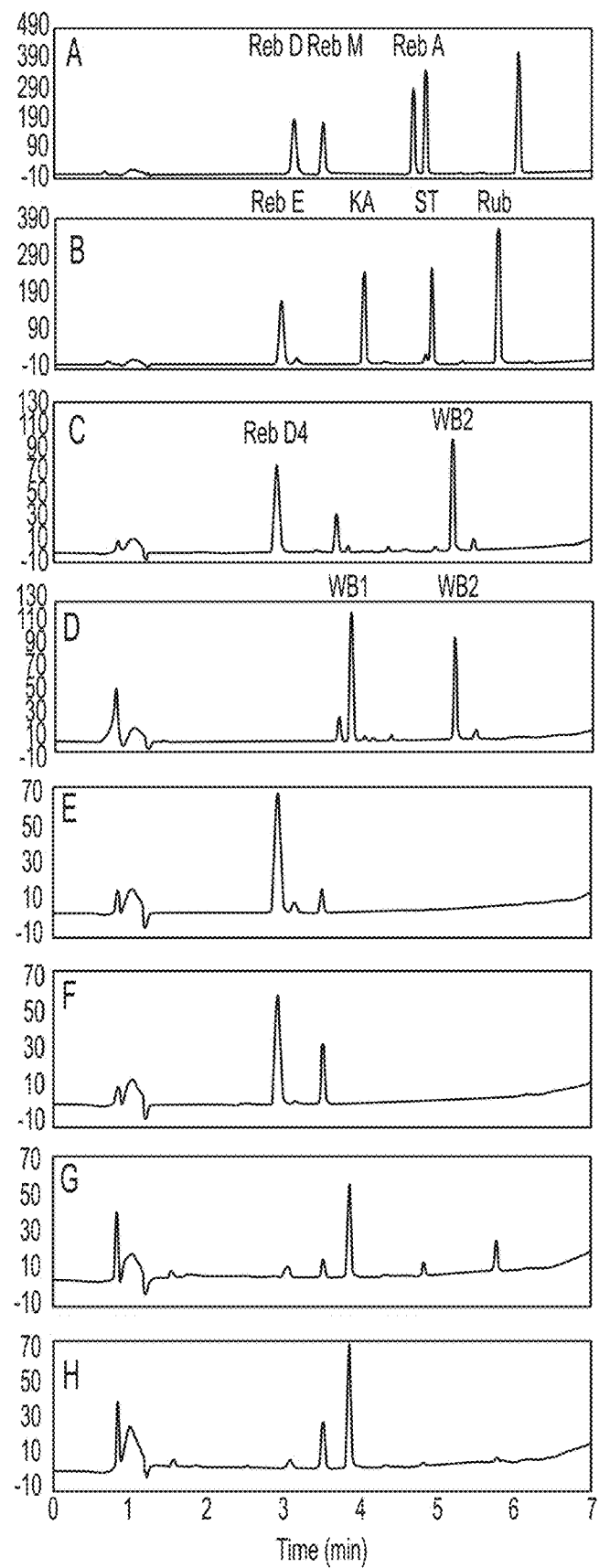
FIG. 6. Shows the Hydrolysis of the produced compound to confirm the bioconversion of Reb E to Reb D4 by C1m2 and C1m3 mutant. A: shows the standards of rebaudioside D ("Reb D"), rebaudioside M ("Reb M") and rebaudioside A ("Reb A"). B: shows the standards of rebaudioside E ("Reb E"), rebaudioside KA("KA"), Stevioside ("ST") and rubusoside ("Rub"). C: shows the standard of rebaudioside D4 ("Reb D4") and Reb WB2 ("WB2") D: shows the standards of rebaudioside WB1 ("WB1") and Reb WB2 ("WB2"). Bioconversion of Reb E by C1m2 (E) and C1m3 (F) at 16 hr. Hydrolysis of produced compounds by GXT6 at 16 hr. G: shows hydrolysis of produced compounds in C1m2 reaction, H: shows hydrolysis of produced compound in C1m3 reaction.

The same enzymatic reaction was run using the produced compounds from Reb E bioconversion by C1m2 and C1m3. As shown in FIG. 6, Reb WB1 only can be produced in C1m2 and C1m3 reactions. Less or no Reb A and rubusoside can be produced in C1m2 and C1m3 reactions. These results provided the evidence to confirm the biosynthesis of Reb D4 in C1m2 and C1m3 reaction. C1m2 and C1m3 has the main enzymatic activity for conversion of Reb E to Reb D4, less or no activity for conversion of Reb E to Reb D.

According to the current disclosure, Reb E was hydrolyzed by the action of the C1m2 and C1m3 enzymes to produce Reb M. In each of the measurements taken the compounds were produced along with what the biosynthetic pathway of the current disclosure would predict.

5. Bioconversion of Stevioside to Reb D4 by Enzymatic Reaction

To confirm the conversion of stevioside to rebaudioside D4 in vitro, the HV1, C1m2 and C1m3 enzymes were assayed using stevioside as the steviol glycoside substrate. The reaction system contained 50 mM potassium phosphate buffer (pH 7.2), 3 mM $MgCl_2$, 1 mg/ml stevioside, 1 mM UDP-glucose, HV1 and C1m2 or C1m3. The reaction was performed at 37° C. and terminated by adding 1-butanol. The samples were extracted three times with 1-butanol. The pooled fraction was dried and dissolved in 80% methanol for high-performance liquid chromatography (HPLC) analysis. HPLC analysis was performed as above description.

Figure 7:
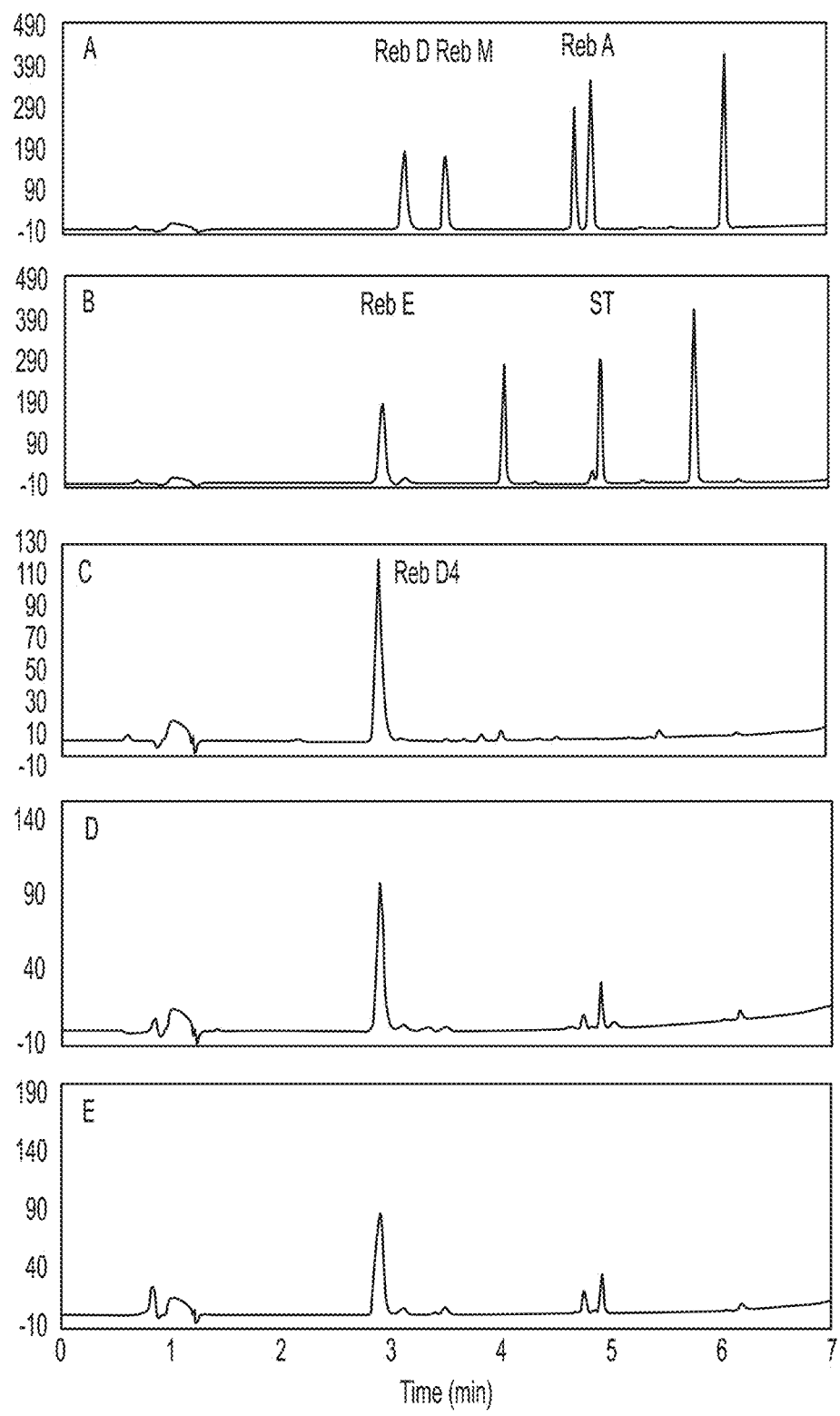
FIG. 7. Shows in vitro production of Reb D4 from stevioside by combination of Hv1 and C1m2 or C1m3 enzyme. A: shows the standards of rebaudioside D ("Reb D"), rebaudioside M ("Reb M") and rebaudioside A ("Reb A"). B: shows the standards of rebaudioside E ("Reb E") and stevioside ("ST"). C: shows the standard of rebaudioside D4 ("Reb D4"). Reb D4 was produced by combination of HV1 with C1m2 (D) or C1m3(E) at 16 hr.
Figure 8:
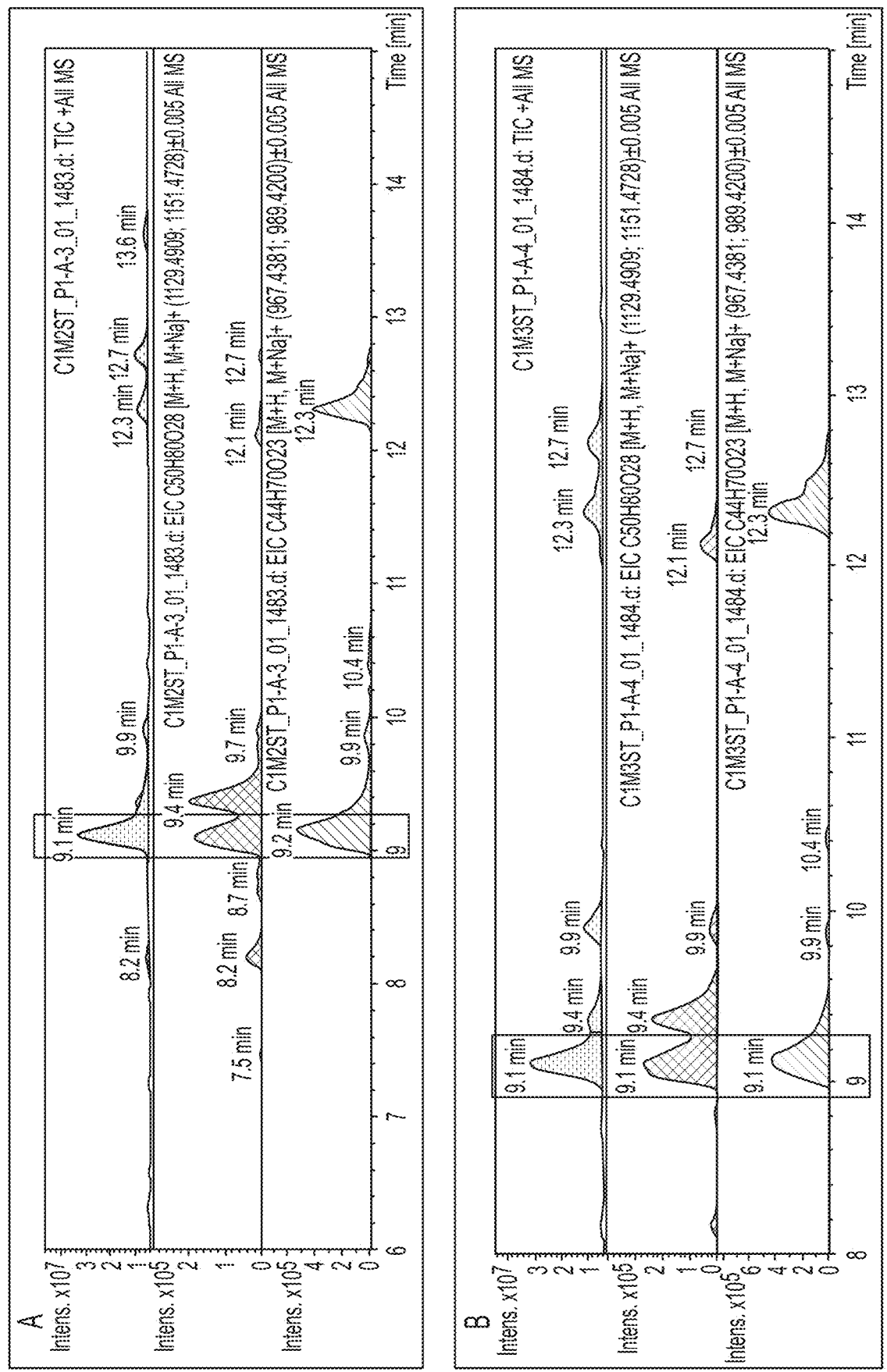
FIG. 8. Shows the LC-MS Analysis of the produced Reb D4 by combination of HV1 with C1m2 (A) or C1m3 (B).

As shown in FIG. 7, the combination of HV1 with C1m2 or C1m3 can convert stevioside to Reb D4. In the reactions, stevioside can be converted to Reb E by HV1 enzyme, then the produced Reb E can be converted to Reb D4 by C1m2 or C1m3 enzyme. In order to identify Reb D4 compound in the related reactions, samples were analyzed by LC-MS using the Synergy Hydro-RP column. As shown in FIG. 8, the produced compound (retention time 9.1 min) has the same molecular weight as Reb D4. Reb E substrate also can be detected at the same retention time. These results provide the evidence supporting Reb D4 production in the reactions.

Figure 9:
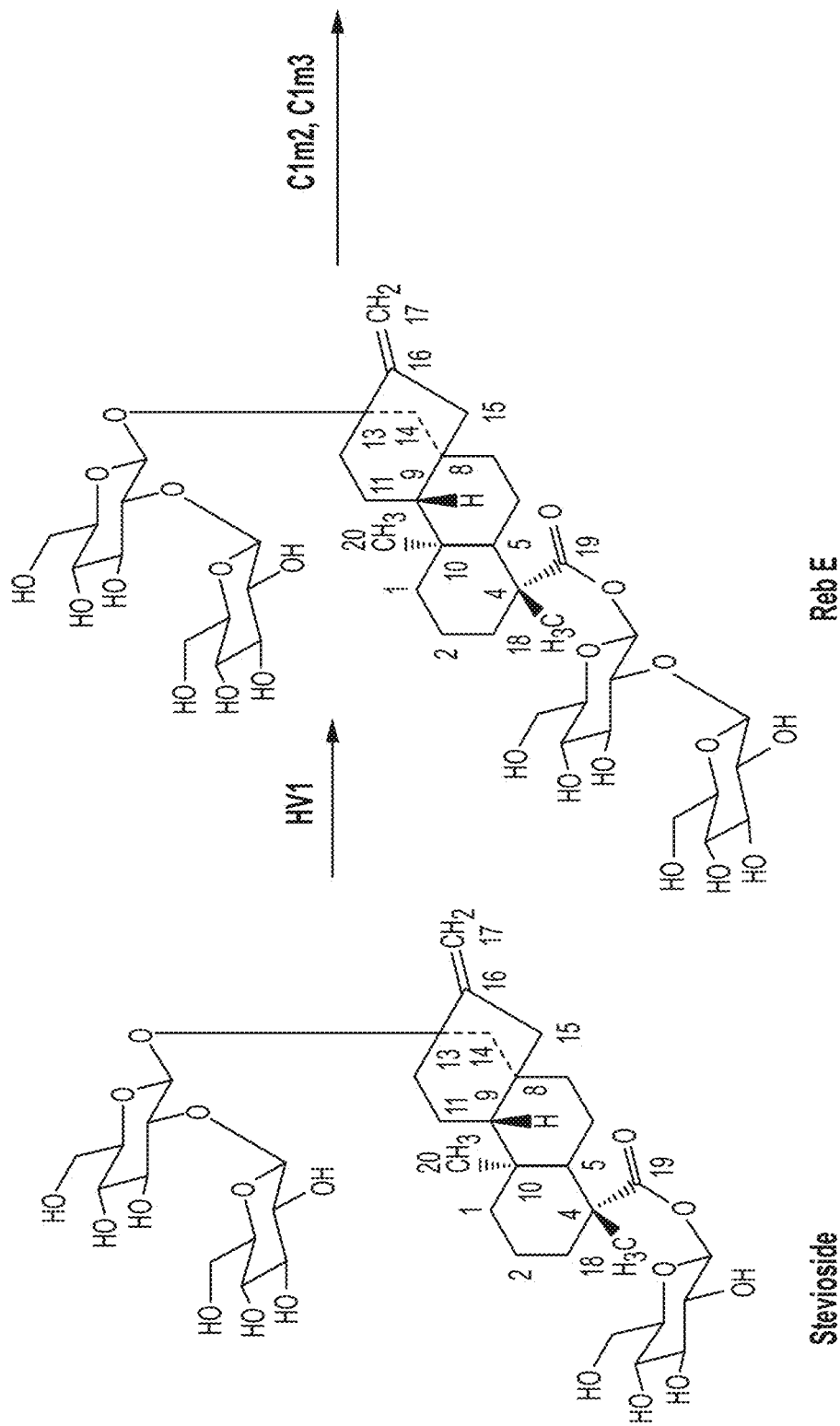
FIG. 9. Shows a Biosynthetic Pathway of Reb M from stevioside.
Figure 9:
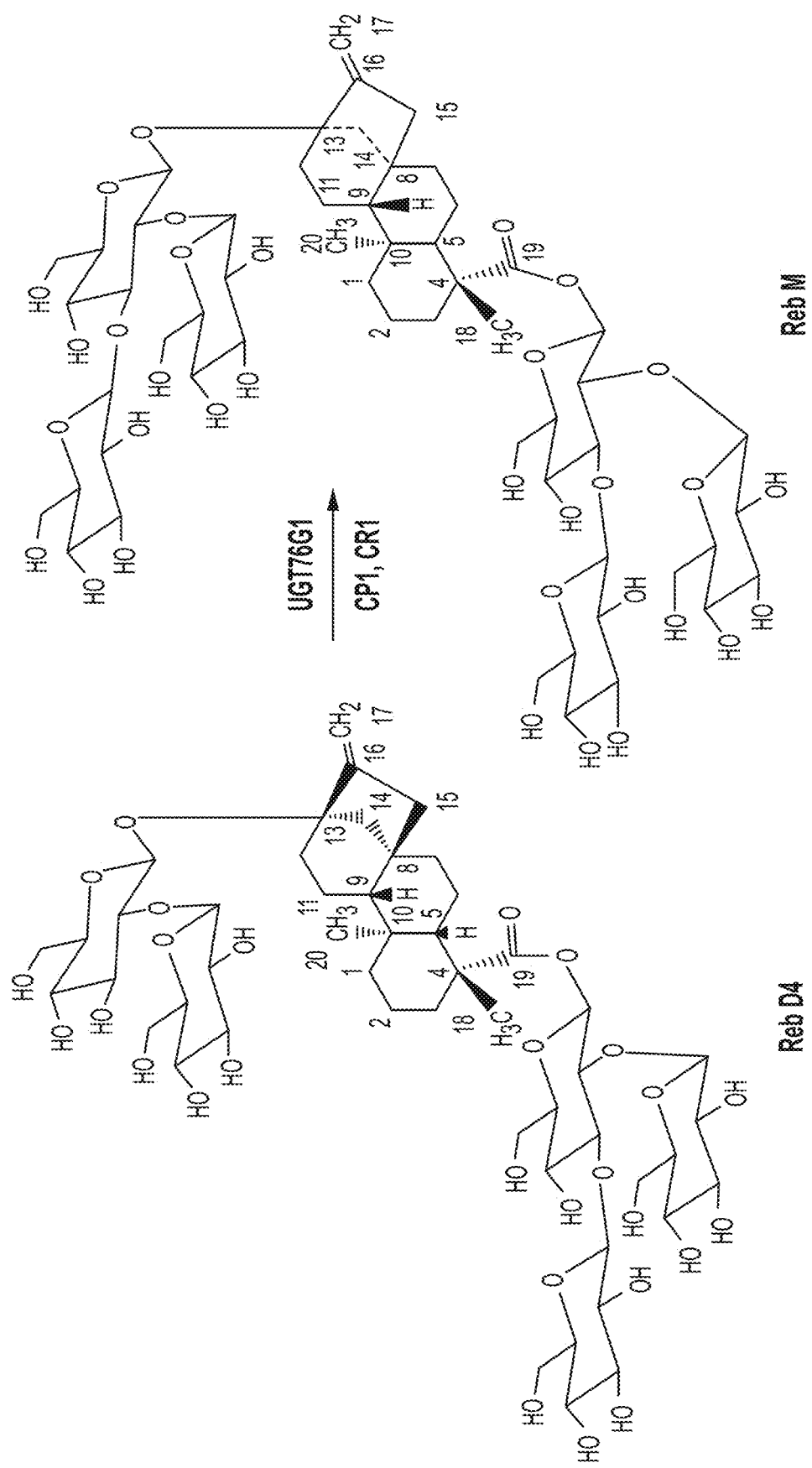
Figure 10:
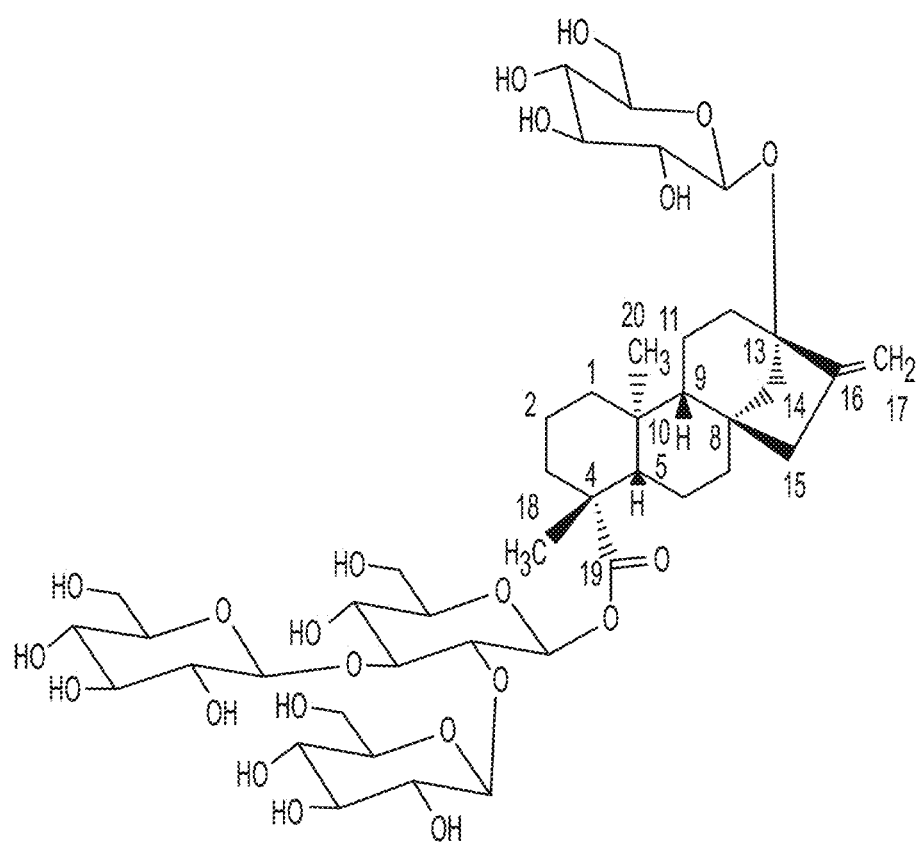
FIG. 10. Shows the structure of the steviol glycoside WB1.

According to the current disclosure, two UGT mutants were developed that, when put into the bioconversion system, allowed the production of Reb D4 from Reb E. The entire biosynthetic pathway from stevioside to Reb M through Reb D4 was confirmed (FIG. 9). Stevioside can be converted to Reb E by HV1 enzyme as previously described, then Reb E can be converted to Reb D4 by C1m2 or C1m3 enzyme as described herein. Lastly, Reb D4 can be converted to Reb M by one of enzymes from UGT76G1, CP1 and CR1.

UGT mutants were identified for converting Reb E to Reb D4. Based on structure modeling analysis, some mutant variations of the CP1enzyme (which is itself a circular version of UGT76G1) were screened for their capacity to convert Reb E to Reb D4. Two mutants were found to have this capability, they have been identified as C1m2 and C1m3.

As described above, an LC-MS method was established to identify Reb D4 production. As shown in the HPLC profile, the retention time of Reb E and Reb D4 is very close. It is difficult to distinguish Reb E and Reb D4 in the reactions by most existing HPLC methods. To confirm the conversion of Reb E to Reb D4, the produced compound was analyzed by LC-MS analysis. Reb D4 compound can be detected in the bioconversion of Reb E by both the C1m2 and C1m3 enzymes.

As described above, an enzymatic assay was established to confirm Reb D4 production. In order to confirm the production of Reb D4 in the related reactions, a beta-glucosidase assay was generated to distinguish Reb D4, Reb E and Reb D steviol glycosides. In this assay beta-glucosidase can hydrolyze steviol glycosides to remove the glucose group(s). GXT6 has the specific enzymatic activity to hydrolyze Reb D4, Red E and Reb D. So, the enzymatic assay was generated to distinguish the three compounds present in the reactions of the current disclosure. After enzymatic assay, the exist of Reb D4 was confirmed in the related reactions, supporting the enzymatic activity of C1m2 and C1m3 for Reb D4 synthesis from Reb E.

Sequences of Interest:

Sequences:

UGT76G1 sequences:

(SEQ ID NO: 1)
UGT76G1 sequence Amino Acid Sequence:
MENKTETTVRRRRRIILFPVPFQGHINPILQLANVLYSKGFSITIFHTNF
NKPKTSNYPHFTFRFILDNDPQDERISNLPTHGPLAGMRIPRIINEHGAD
ELRRELELLMLASEEDEEVSCLITDALWYFAQSVADSLNLRRINLMTSSL
FNFHAHVSLPQFDELGYLDPDDKTRLEEQASGFPMLKVKDIKSAYSNWQI
LKEILGKMIKQTKASSGVIWNSFKELEESELETVIREIPAPSFLIPLPKH
LTASSSSLLDHDRTVFQWLDQQPPSSVLYVSFGSTSEVDEKDFLEIARGL
VDSKQSFLWVVRPGFVKGSTWVEPLPDGFLGERGRIVKWVPQQEVLAHGA
IGAFWTHSGWNSTLESVCEGVPMIFSDFGLDQPLNARYMSDVLKVGVYLE
NGWERGEIANAIRRVMVDEEGEYIRQNARVLKQKADVSLMKGGSSYESLE
SLVSYISSL UGT76G1 sequence DNA sequence:

(SEQ ID NO: 2)
ATGGAGAATAAGACAGAAACAACCGTAAGACGGAGGCGGAGGATTATCTT
GTTCCCTGTACCATTTCAGGGCCATATTAATCCGATCCTCCAATTAGCAA
ACGTCCTCTACTCCAAGGGATTTTCAATAACAATCTTCCATACTAACTTT
AACAAGCCTAAAACGAGTAATTATCCTCACTTTACATTCAGGTTCATTCT
AGACAACGACCCTCAGGATGAGCGTATCTCAAATTTACCTACGCATGGCC
CCTTGGCAGGTATGCGAATACCAATAATCAATGAGCATGGAGCCGATGAA
CTCCGTCGCGAGTTAGAGCTTCTCATGCTCGCAAGTGAGGAAGACGAGGA
AGTTTCGTGCCTAATAACTGATGCGCTTTGGTACTTCGCCCAATCAGTCG
CAGACTCACTGAATCTACGCCGTTTGGTCCTTATGACAAGTTCATTATTC
AACTTTCACGCACATGTATCACTGCCGCAATTTGACGAGTTGGGTTACCT
GGACCCGGATGACAAAACGCGATTGGAGGAACAAGCGTCGGGCTTCCCCA
TGCTGAAAGTCAAAGATATTAAGAGCGCTTATAGTAATTGGCAAATTCTG
AAAGAAATTCTCGGAAAAATGATAAAGCAAACCAAAGCGTCCTCTGGAGT
AATCTGGAACTCCTTCAAGGAGTTAGAGGAATCTGAACTTGAAACGTCA
TCAGAGAAATCCCCGCTCCCTCGTTCTTAATTCCACTACCCAAGCACCTT
ACTGCAAGTAGCAGTTCCCTCCTAGATCATGACCGAACCGTGTTTCAGTG
GCTGGATCAGCAACCCCCGTCGTCAGTTCTATATGTAAGCTTTGGGAGTA
CTTCGGAAGTGGATGAAAAGGACTTCTTAGAGATTGCGCGAGGGCTCGTG
GATAGCAAACAGAGCTTCCTGTGGGTAGTGAGACCGGGATTCGTTAAGGG
CTCGACGTGGGTCGAGCCGTTGCCAGATGGTTTTCTAGGGGAGAGAGGGA
GAATCGTGAAATGGGTTCCACAGCAAGAGGTTTTGGCTCACGGAGCTATA
GGGGCTTTTGGACCCACTCGGTTGGAATTCTACTCTTGAAAGTGTCTG
TGAAGGCGTTCCAATGATATTTTCTGATTTTGGGCTTGACCAGCCTCTAA
ACGCTCGCTATATGTCTGATGTGTTGAAGGTTGGCGTGTACCTGGAGAAT
GGTTGGGAAAGGGGGGAAATTGCCAACGCCATACGCCGGGTAATGGTGGA
CGAGGAAGGTGAGTACATACGTCAGAACGCTCGGGTTTTAAAACAAAAAG
CGGACGTCAGCCTTATGAAGGGAGGTAGCTCCTATGAATCCCTAGAATCC
TTGGTAAGCTATATATCTTCGTTATAA

CP1 sequences:

(SEQ ID NO: 3)
CP1 sequence Amino Acid:
MNWQILKEILGKMIKQTKASSGVIWNSFKELEESELETVIREIPAPSFLI
PLPKHLTASSSSLLDHDRTVFQWLDQQPPSSVLYVSFGSTSEVDEKDFLE
IARGLVDSKQSFLWVVRPGFVKGSTWVEPLPDGFLGERGRIVKWVPQQEV
LAHGAIGAFWTHSGWNSTLESVCEGVPMIFSDFGLDQPLNARYMSDVILK
VGVYLENGWERGEIANAIRRVMVDEEGEYIRQNARVLKQKADVSLMKGGS
SYESLESLVSYISSLENKTETTVRRRRRIILFPVPFQGHINPILQLANVL
YSKGESITIFHTNFNKPKTSNYPHFTFRFILDNDPQDERISNLPTHGPLA
GMRIPIINEHGADELRRELELLMLASEEDEEVSCLITDALWYFAQSVADS
LNLRRLVLMTSSLFNFHAHVSLPQFDELGYLDPDDKTRLEEQASGFPMLK
VKDIKSAYS CP1 sequence DNA sequence:

(SEQ ID NO: 4)
ATGAACCTGCAAATCCTGAAAGAAATCCTGGGTAAAATGATCAAACAAAC
CAAAGCGTCGTCGGGCGTTATCTGGAACTCCTTCAAAGAACTGGAAGAAT
CAGAACTGGAAACCGTTATTCGCGAAATCCCGGCTCCGTCGTTCCTGATT
CCGCTGCCGAAACATCTGACCGCGAGCAGCAGCAGCCTGCTGGATCACGA
CCGTACGGTCTTTCAGTGGCTGGATCAGCAACCGCCGTCATCGGTGCTGT
ATGTTTCATTCGGTAGCACCTCTGAAGTCGATGAAAAAGACTTTCTGGAA
ATCGCTCGCGGCCTGGTGGATAGTAAACAGTCCTTCCTGTGGGTGGTTCG
TCCGGGTTTTGTGAAAGGCAGCACGTGGGTTGAACCGCTGCCGGATGGCT
TCCTGGGTGAACGCGGCCGTATTGTCAAATGGGTGCCGCAGCAAGAAGTG
CTGGCACATGGTGCTATCGGCGCGTTTTGGACCCACTCTGGTTGGAACAG
TACGCTGGAATCCGTTTGCGAAGGTGTCCCGATGATTTTCAGCGATTTTG
GCCTGGACCAGCCGCTGAATGCCCGCTATATGTCTGATGTTCTGAAAGTC
GGTGTGTACCTGGAAAACGGTTGGGAACGTGGCGAAATTGCGAATGCCAT
CCGTCGCGTTATGGTCGATGAAGAAGGCGAATACATTCGCCAGAACGCTC
GTGTCCTGAAACAAAAAGCGGACGTGAGCCTGATGAAAGGCGGTAGCTCT
TATGAATCACTGGAATCCGTGGTTAGCTACATCAGTTCCCTGGAAAATAA
AACCGAAACCACGGTGCGTCGCCGTCGCCGTATTATCCTGTTCCCGGTTC
CGTTTCAGGGTCATATTAACCCGATCCTGCAACTGGCGAATGTTCTGTAT
TCAAAAGGCTTTTCGATCACCATCTTCCATACGAACTTCAACAAACCGAA
AACCAGTAACTACCCGCACTTTACGTTCCGCTTTATTCTGGATAACGACC
CGCAGGATGAACGTATCTCCAATCTGCCGACCCACGGCCCGCTGGCCGGT
ATGCGCATTCCGATTATCAATGAACACGGTGCAGATGAACTGCGCCGTGA
ACTGGAACTGCTGATGCTGGCCAGTGAAGAAGATGAAGAAGTGTCCTGTC
CTTGATCACCGACGCAGTGGTATTTCGCCCAGAGCGTTGCAGATTCTCTG
AACCTGCGCCGTCTGGTCCTGATGACGTCATCGCTGTTCAATTTTCATGC

Sequences:

GCACGTTTCTCTGCCGCAATTTGATGAACTGGGCTACCTGGACCCGGATG
ACAAAACCCGTCTGGAAGAACAAGCCAGTGGTTTTCCGATGCTGAAAGTC
AAAGACATTAAATCCGCCTATTCGTAA

GXT6: amino acid. From Streptomyces sp. GXT6
(SEQ ID NO: 5)
MTPPFGSELALPETFLMGAATSAHQVEGNNIGSDWWEIEHRPDTFVAQPS
GDAADSYHRWPEDMDLLAGLGFNAYRFSIEWARIEPEPGRISRAALAHYR
AMVRGALERGLTPLVTLHFTFTCPRWFSARGGWLAPDAAETFTAYARTAS
EVVGEGVSHVATINEPNMLAHMYTLRRLAAEHGWSALAEGRRAGAAAFDP
AAVAPDRDVTAALIEAHRRSAVVLRQAGLQVGWTVANQVYHAEPGAEEIA
TAYARPREDVFLEAAREDDWIGVQAYTRHRIGPDGPLPVPDGAPTTLTGW
EVYPDALAEAVLHTVATVGAQVPVIVTENGIATGDDDQRIAYTRQALAGL
ARVMREGADVRGYFHWSALDNYEWGTYRPTFGLIGVDPDTFARTPKPSAR
WLGALARDRRLPAAKAPVGTGAPTAR GXT6: DNA Codon optimization for E coli
(SEQ ID NO: 6)
ATGACCCCACCGTTTGGTAGCGAACTGGCGCTTCCGGAAACATTCCTTAT
GGGTGCGGCCACTTCAGCTCACCAGGTTGAAGGTAATAATATCGGTAGCG
ATTGGTGGGAAATTGAGCACCGCCCGGATACTTTTGTTGCTCAGCCGTCC
GGAGATGCGGCAGATTCCTATCACCGCTGGCCGGAAGATATGGATTTGCT
TGCCGGATTGGGCTTTAATGCTTATCGTTTTAGTATTGAGTGGGCTCGTA
TTGAACCGGAACCTGGTCGGATTTCAAGAGCGGCTCTGGCGCATTATCGT
GCGATGGTCCGCGGAGCGCTGGAGCGTGGCCTGACACCATTAGTAACTTT
GCATCACTTTACATGCCCACGGTGGTTTTCAGCTCGGGGCGGTTGGTTAG
CTCCAGATGCAGCGGAAACTTTTACTGCTTATGCCAGAACTGCCAGCGAG
GTAGTTGGTGAGGGCGTGTCTCATGTCGCGACGATCAACGAGCGTAACAT
GCTGGCACATATGTATACTTTGAGAAGACTTGCAGCGGAACACGGTTGGT
CAGCCTTAGCGAAGGAAGACGTCTGGCGCCGCAGCTTTTGATCGGCT
GCTGTTGCCCCGGATCGCGATGTGACGGCTGCTCTGATTGAGGCGCACCG
TCGCAGCGCCGTAGTGCTGCGCCAGGCCGGCCTGCAGGTTGGCTGGACGG
TTGCCAATCAGGTTTATCACGCCGAACCGGGAGCAGAAGAAATTGCTACG
GCCTATGCTCGGCCACGGGAGGATGTATTCTTGGAGGCAGCCCGCGAAGA
TGATTGGATCGGCGTGCAGGCATATACTCGTCACCGTATTGGACCGGATG
GACCTCTGCCGGTACCTGATGGGGCACCTACAACACTTACTGGCTGGGAA
GTTTATCCTGATGCCCTTGCAGAAGCCGTGCTGCATACAGTCGCCACCGT
GGGTGCGCAGGTACCAGTTATTGTAACAGAGAATGGTATCGCCACCGGCG
ATGATGATCAGCGTATCGCATATACTAGACAGGCACTGGCAGGGTTGGCC
CGTGTCATGCGCGAAGGTGCGGATGTGCGGGGATATTTTCATTGGTCGC
ATTAGATAACTATGAATGGGGCACCTATCGTCAACCTTCGGGTTAATCG
GGGTTGATCCGGATACGTTTGCTCGGACGCCTAAACCTTCTGCACGCTGG
CTGGGTGCTCTGGCACGCGATCGCAGACTGCCAGCCGCGAAAGCGCCTGT
CGGCACTGGCGCCCCTACAGCTCGC C1m2: Amino Acid Sequence for mutant enzyme
(SEQ ID NO: 7)
MNWQIAKEILGKIMIKQTKASSGVPIWNSFKELEESELETVIREIPAPSF
LIPLPKHLTASSSSLLDHDRTVFQWLDQQPPSSVLYVSFGSASEVDEKDF
FLEIARGLVDSKQSFLWVVRPGVKGSTWVEPLPDGFLGERGRIVKWVPQQ
EVLAHGAIGAFWTHSGWNSTLESVCEGVPMIFSDFGGDQPLNARYMSDVI
LKVGVYLENGWERGEIANAIRRVMVDEEGEYIRQNARVLKQKADVSLMKG
GSSYESLESLVSYISSLENKTETTVRRRRRIILFPVPFQGHINPILQLAN
VLYSKGFSITIFHTNFNKPKTSNYPHFTFRFILDNDPQDERISNLPTHGP
LAGMRIPIINEHGADELRRELELLMLASEEDEEVSCLITDALWYFAQSVA
DSLNLRRLVLMTSSLFNMFHAHVSLPQFDELGYLDPDDKTRLEEQASGFPM
LKVKDIKSAYS C1M2: DNA Sequence for mutant enzyme
(SEQ ID NO: 8)
ATGAACTGGCAAATCGCGAAAGAAATCCTGGGTAAAATGATCAAACAAAC
CAAAGCGTCGTCGGGCGTTATCTGGAACTCCTTCAAAGAACTGGAAGAAT
CAGAACTGGAAACCGTTATTCGCGAAATCCCGGCTCCGTCGTTCCTGATT
CCGCTGCCGAAACATCTGACCGCGAGCAGCAGCAGCCTGCTGGATCACGA
TCGTACGGTCTTTCAGTGGCTGGATCAGCAACCGCCGTCATCGGTGCTGT
ATGTTTCATTCGGTAGCACCTCTGAAGTCGATGAAGAAGACTTTCTGGAA
ATCGCTCGCGGCCTGGTGGATAGTAAACAGTCCTTCCTGTGGGTGGTTCG
TCCGGGTTTTGTGAAAGGCAGCACGTGGGTTGAACCGCTGCCGGATGGCT
TCCTGGGTGAACGCGGCCGTATTGTCAAATGGGTGCCGCAGCAAGAAGTG
CTGGCACATGGTGCTATCGGCGCGTTTGGACCCACTCTGGTTGAACAG
TACGCTGGAATCCGTTTGCGAAGGTGTCCCGATGATTTTCAGCGATTTTG
GCGGCGACCAGCCGCTGAATGCCCGCTATATGTCTGATGTCTGAAAGTC
GGTGTGTACCTGGAAAACGGTTGGGAACGTGGCGAAATTGCGAATGCCAT
CCGTCGCGTTATGGTCGATGAAGAAGGCGAATACATTCGCCAGAACGCT
CGTGTCCGTGAAACAAAAGCGGACGTGAGCCTGATGAAAGGCGGTAGCTC
CTTATGAATCACTGGAATCGCTGGTTAGCTACATCAGTTCCCTGGAAAAT
AAACCGAAACCACGGTGCGTCGCCGTCGCCGTATTATCCTGTTCCCGGT TCCGTTTCAGGGTCATATTAACCCGATCCTGCAACTGGCGAATGTCTGTA
TTCAAAAGGCTTTTCGATCACCATCTTCCATACGAACTTCAACAAACCGA
AAACCAGTAACTACCCCGCACTTTACGTTCCGTTTATTCTGGATAACGACC
CGCAGGATGAACGTATCTCCAATCTGCCGACCCACGGCCCGCTGGCCGGT
ATGCGCATTCCGATTATCAATGAACACGGTGCAGATGAACTGCGCCGTGA
ACTGGAACTGCTGATGCTGGCCAGTGAAGAAGATGAAGAAGTGTCCTGTC
TGATCACCGACGCACTGTGGTATTTCGCCCAGAGCGTTGCAGATTCTCTG
AACCTGCGCCGTCTGGTCCTGATGACGTCATCGCTGTTCAATTTTCATGC
GCACGTTTCTCTGCCGCAATTTGATGAACTGGGCTACCTGGACCCGGATG
ACAAAACCCGTCTGGAAGAACAAGCCAGTGGTTTTCCGATGCTGAAAGTC
AAAGACATTAAATCCGCCTATTCGTAA C1m3: Amino Acid Sequence for mutant enzyme
(SEQ ID NO: 9)
MNWQIAKEILGKMIKQTKASSGVIWNSFKELEESELETVIREIPAPSFLI
PLPKHLTASSSSLLDHDRTVFQWLDQQPPSSVLYVSFGSASEVDEKDFLE
IARGLVDSKQSFLWVVRPGVKGSTWVEPLPDGFLGERGRIVKWVPQQEV
LAHGAIGAFWTHSGWNSTLESVCEGVPMIFSDFGGDQPLNARYMSDVLKV
GVYLENGWERGEIANAIRRVMVDEEGEYIRQNARVLKQKADVSLMKGGSS
YESLESLVSYISSLENKTETTVRRRRRIILFPVPFQGHINPILQLANVLY
SKGFSITIFHTNFNKPKTSNYPHFTFRFILDNDPQDERISNLPTHGPLAG
MRIPIINEHGADELRRELELLMLASEEDEEVSCLITDALWYFAQSVADSL
NLRRLVLMTSSLFNMFHAHVSLPQFDELGYLDPDDKTRLEEQASGFPMLK
VKDIKSAYS C1m3: DNA Sequence for mutant enzyme
(SEQ ID NO: 10)
ATGAACTGGCAAATCGCGAAAGAAATCCTGGGTAAAATGATCAAACAAAC
CAAAGCGTCGTCGGGCGTTATCTGGAACTCCTTCAAAGAACTGGAAGAAT
CAGAACTGGAAACCGTTATTCGCGAAATCCCGGCTCCGTCGTTCCTGATT
CCGCTGCCGAAACATCTGACCGCGAGCAGCAGCAGCCTGCTGGATCACGA
TCGTACGGTCTTTCAGTGGCTGGATCAGCAACCGCCGTCATCGGTGCTGT
ATGTTTCATTCGGTAGCGCCTCTGAAGTCGATGAAGAAAGACTTTCTGGAA
ATCGCTCGCGGCCTGGTGGATAGTAAACAGTCCTTCCTGTGGGTGGTTCG
TCCGGGTTTTGTGAAAGGCAGCACGTGGGTTGAACCGCTGCCGGATGGCT
TCCTGGGTGAACGCGGCCGTATTGTCAAATGGGTGCCGCAGCAAGAAGTG
CTGGCACATGGTGCTATCGGCGCGTTTTGGACCCACTCTGGTTGAACAG
TACGCTGGAATCCGTTTGCGAAGGTGTCCCGATGATTTTCAGCGATTTTG
GCGGCGACCAGCCGCTGAATGCCCGCTATATGTCTGATGTTCTGAAAGTCGGTG
TGCGTGGGAAAACGGTTGGGAACGTGGCGAAATTGCGAATGCCATCCGTCG
CGTTATGGTCGATGAAGAAGGCGAATACATTCGCCAGAACGCTC
GTGTCCTGAAACAAAAAGCGGACGTGAGCCTGATGAAAGGCGGTAGCTCT
TATGAATCACTGGAATCGCTGGTTAGCTACATCAGTTCCCTGGAAAATAA
AACCGAAACCACGGTGCGTCGCCGTCGCCGTATTATCCTGTTCCCGGTTC
CGTTTCAGGGTCATATTAACCCGATCCTGCAACTGGCGAATGTTCTGTAT
TCAAAAGGCTTTTCGATCACCATCTTCCATACGAACTTCAACAAACCGAA
AACCAGTAACTACCCGCACTTTACGTTCCGCTTTATTCTGGATAACGACC
CGCAGGATGAACGTATCTCCAATCTGCCGACCCACGGCCCGCTGGCCGGT
ATGCGCATTCCGATTATCAATGAACACGGTGCAGATGAACTGCGCCGTGA
ACTGGAACTGCTGATGCTGGCCAGTGAAGAAGATGAAGAAGTGTCCTGTC
TGATCACCGACGCACTGTGGTATTTCGCCCAGAGCGTTGCAGATTCTCTG
AACCTGCGCCGTCTGGTCCTGATGACGTCATCGCTGTTCAATTTTCATGC
GCACGTTTCTCTGCCGCAATTTGATGAACTGGGCTACCTGGACCCGGATG
ACAAAACCCGTCTGGAAGAACAAGCCAGTGGTTTTCCGATGCTGAAAGTC
AAAGACATTAAATCCGCCTATTCGTAA HV1: Amino Acid Sequence
(SEQ. ID NO: 11)
MDGNSSSPLHVVICPWLALGHLLPCLDIAERLASRGHRVSFVSTPRNIA
RLPPLRPAVAPLVDFVALPLPHVDGLPEGAESTNDVPYDKFELHRKAFDG
LAAPFSEFLRAACAEGAGSRPDWLIVDTFHHWAAAAAVENKVPCVMLLLG
AATVIAGFARGVSEHAAAAVGKERPAAEAPSFETERRKLMTTQNASGMTV
AERYFLTLMRSDLVAIRSCAEWEPESVAALTTLAGKPVVPLGLLPPSPEG
HGRGVSKEDAAVRWLDAQPAKSVVYALGSEVPLRAEQVELALGLELSGA
RFLWALRKPTDAPDAAVLPPGFEERTRGRGLVVTGWVPQIGVLAHGAVAA
FLTHCGWNSTIEGLLFGHPLIMLPISSDQGPNARLMEGRKGMQVPRDESD
GSFRIZEDVAATVRAVAVEEDGRRVFTANAKKMQEIVADGACHERCIDGG
IQQLRSYKA HV1: DNA Sequence
(SEQ ID NO: 12)
ATGGATGGTAACTCCTCCTCCTCGCCGCTGCATGTGGTCATTTGTCCGTG
GCTGGCTCTGGGTCACCTGCTGCCGTGTCTGGATATTGCTGAACGTCTGG
CGTCACGCGGCCATCGTGTCAGTTTTGTGTCCACCCCGCGCAACATTGCC
CGTCTGCCGCCGCTGCGTCCGGCTGTTGCACCGCTGGTTGATTTCGTCGC
ACTGCCGCTGCCGCATGTTGACGGTCTGCCGGAGGGTGCGCAAATCGACC
AATGATGTGCCGTATGACAAATTTGAACTGCACCGTAAGGCGTTCGATGG Sequences:

```
TCTGGCGGCCCCGTTTAGCGAATTTCTGCGTGCAGCTTGCGCAGAAGGTG
CAGGTTCTCGCCCGGATTGGCTGATTGTGGACACCTTTCATCACTGGGCG
GCGGCGGCCGGCGGTGGAAAACAAAGTGCCGTGTGTTATGCTGCTGCTGG
TGCAGCAACGGTGATCGCTGGTTTCGCGCGTGGTGTTAGCGAACATGCGG
CGGCGGCGGTGGGTAAAGAACGTCCGGCTGCGGAAGCCCCGAGTTTTGAA
ACCGAACGTCGCAAGCTGATGACCACGCAGAATGCCTCCGGCATGACCGT
GGCAGAACGCTATTTCCTGACGCTGATGCGTAGCGATCTGGTTGCCATCC
GCTCTTGCGCAGAATGGGAACCGGAAAGCGTGGCAGCACTGACCACGCTG
GCAGGTAAACCGGTGGTTCCGCTGGGTCTGCTGCCGCCGAGTCCGGAAGG
CGGTCGTGGCGTTTCCAAAGAAGATGCTGCGGTCCGTTGGCTGGACGCAC
AGCCGGCAAAGTCAGTCGTGTACGTCGCACTGGGTTCGGAAGTGCCGCTG
CGTGCGGAACAAGTTCACGAACTGGCACTGGGCCTGGAACTGAGCGGTGC
TCGCTTTCTGTGGGCGCTCGTAAACCGACCGATGCACCGGACGCCGCAGT
GCTGCCGCCGGGTTTCGAAGAACGTACCCGCGGCCGTGGTCTGGTTGTCA
CGGGTTGGGTGCCGCAGATTGGCGTTCTGGCTCATGGTGCGGTGGCTGCG
TTTCTGACCCACTGTGGCTGGAACTCTACGATCGAAGGCCTGCTGTTCGG
TCATCCGCTGATTATGCTGCCGATCAGCTCTGATCAGGGTCCGAATGCGC
GCCTGATGGAAGGCCGTAAAGTCGGTATGCAAGTGCCGCGTGATGAATCA
GACGGCTCGTTTCGTCGCGAAGATGTTGCCGCAACCGTCCGCGCCGTGGC
AGTTGAAGAAGACGGTCGTCGCGTCTTCACGGCTAACGCGAAAAAGATGC
AAGAAATTGTGGCCGATGGCGCATGCCACGAACGTTGTATTGACGGTTTT
ATCCAGCAACTGCGCAGTTACAAGGCGTAA

CR1: Amino acid sequence
                                       (SEQ ID NO: 13)
MNWQIAKEILGKMIKQTKASSGVIWNSFKELEESELETVIREIPAPSFLI
PLPKHLTASSSSLLDHDRTVFQWLDQQPPSSVLYVSFGSTSEVDEKDFLE
IARGLVDSKQSFLWVVRPGFVKGSTWVEPLPDGFLGERGRIVKWVPQQEV
LAHGAIGAFWTHSGWNSTLESVCEGVPMIFSDFGLDQPLNARYMSDVLKV
GVYLENGWERGEIANAIRRVMVDEEGEYIRQNARVLKQKADVSLMKGGSS
YESLESLVSYISSLENKTETTVRRRRRIILFPVPFQGHINPILQLANVLY
SKGFSITIFHTNFNKPKTSNYPHFTFRFILDNDPQDERISNLPTHGPLAG
MRIPIINEHGADELRRELELLMLASEEDEEVSCLITDALWYFAQSVADSL
NLRRLVLMTSSLFNFHAHVSLPQFDELGYLDPDDKTRLEEQASGFPMLKV
KDIKSAYS CR1: DNA sequence
                                       (SEQ ID NO: 14)
ATGAACTGGCAAATCGCGAAAGAAATCCTGGGTAAAATGATCAAACAAAC
CAAAGCGTCGTCGGGCGTTATCTGGAACTCCTTCAAAGAACTGGAAGAAT
CAGAACTGGAAACCGTTATTCGCGAAATCCCGGCTCCGTCGTTCCTGATT
CCGCTGCCGAAACATCTGACCGCGAGCAGCAGCAGCCTGCTGGATCACGA
CCGTACGGTCTTTCAGTGGCTGGATCAGCAACCGCCGTCATCGGTGCTGT
ATGTTTCATTCGGTAGCACCTCTGAAGTCGATGAAAAAGACTTTCTGGAA
ATCGCTCGCGGCCTGGTGGATAGTAAACAGTCCTTCCTGTGGGTGGTTCG
TCCGGGTTTTGTGAAAGGCAGCACGTGGGTTGAACCGCTGCCGGATGGCT
TCCTGGGTGAACGCGGCCGTATTGTCAAATGGGTGCCGCAGCAAGAAGTG
CTGGCACATGGTGCTATCGGCGCGTTTTGGACCCACTCTGGTTGGAACAG
TACGCTGGAATCCGTTTGCGAAGGTGTCCCGATGATTTTCAGCGACTTTG
GCCTGGACCAGCCGCTGAATGCCCGCTATATGTCTGATGTTCTGAAAGTC
GGTGTGTACCTGGAAAACGGTTGGGAACGTGGCGAAATTGCGAATGCCAT
CCGTCGCGTTATGGTCGATGAAGAAGGCGAATACATTCGCCAGAACGCTC
GTGTCCTGAAACAAAAAGCGGACGTGAGCCTGATGAAAGGCGGTAGCTCT
TATGAATCACTGGAATCGCTGGTTAGCTACATCAGTTCCCTGGAAAATAA
AACCGAAACCACGGTGCGTCGCCGTCGCCGTATTATCCTGTTCCCGGTTC
CGTTTCAGGGTCATATTAACCCGATCCTGCAACTGGCGAATGTTCTGTAT
TCAAAAGGCTTTTCGATCACCATCTTCCATACGAACTTCAACAAACCGAA
AACCAGTAACTACCCGCACTTTACGTTCCGCTTTATTCTGATAACGACCC
GCAGGATGAACGTATCTCCAATCTGCCGACCCACGGCCCGCTGGCCGGTA
TGCGCATTCCGATTATCAATGAACACGGTGCAGATGAACTGCGCCGTGAA
CTGGAACTGCTGATGCTGGCCAGTGAAGAAGATGAAGAAGTGTCCTGTCT
GATCACCGACGCACTGTGGTATTTCGCCCAGAGCGTTGCAGATTCTCTGA
ACCTGCGCCGTCTGGTCCTGATGACGTCATCGCTGTTCAATTTTCATGCG
CACGTTTCTCTGCCGCAATTTGATGAACTGGGCTACCTGGACCCGGATGA
CAAAACCCGTCTGGAAGAACAAGCCAGTGGTTTTCCGATGCTGAAAGTCA
AAGACATTAAATCCGCCTATTCGTAA
```

STATEMENT OF INDUSTRIAL APPLICABILITY/TECHNICAL FIELD

This disclosure has applicability in the food, feed, beverage, and pharmacological industries. This disclosure relates generally to a method for the biosynthetic production of steviol glycosides, e.g., via a modified microbial strain.

LITERATURE CITED AND INCORPORATED BY REFERENCE

1. Brandle, J. E. et al., (1998). *Stevia Rebaudiana: Its Agricultural, Biological, and Chemical Properties*, CANADIAN J. PLANT SCIENCE. 78 (4): 527-36.
2. Ceunen, S., and J. M. C. Geuns, *Steviol Glycosides: Chemical Diversity, Metabolism, and Function*, J. NAT. PROD., 2013, 76 (6), pp 1201-28 (2013).
3. Du J et al., (2011), *Engineering microbial factories for synthesis of value-added products*, J IND MICROBIOL BIOTECHNOL. 38: 873-90.
4. GRAS Notices, USA Food and Drug Administration, United States Health & Human Services. (2016) (relevant to steviol glycosides & polyglycosides).
5. Häusler A, and Münch T., (1997), *Microbial production of natural flavors*, ASM NEWS 63:551-59.
6. Prakash I., et al.; *Isolation and Characterization of a Novel Rebaudioside M Isomer from a Bioconversion Reaction ref Rebaudioside A and AMR Comparison Studies of Rebaudioside M Isolated from Stevia rebaudiana Bertoni and Stevia rebaudiana Morita*, BIOMOLECULES, 2014 June; 4(2): 374-89. (Published online 2014 Mar. 31. 2014).
7. Prakash I., et al., *Development of Next Generation Stevia Sweetener: Rebaudioside M*, FOODS, 2014, 3:162-175.
8. Richman A., et. al., *Functional genomics uncovers three glucosyltransferases involved in the synthesis of the major sweet glucosides of Stevia rebaudiana*, PLANT J. 2005 January;41(1):56-67.
9. Shockey J M. Et a., (2003), *Arabidopsis contains a large superfamily of acyl-activating enzymes: phylogenetic and biochemical analysis reveals a new class of acyl-coenzyme A synthetases*. PLANT PHYSIOL. 132 1065-76.
10. Wang J., et al., *Pathway mining-based integration of critical enzyme parts for de nova biosynthesis of steviolglycosides sweetener in Escherichia coli*, CELL. RESEARCH (2016) 26:258-61.

What is claimed is:

1. A method of producing rebaudioside D4, the method comprising incubating a substrate with a recombinant polypeptide comprising an amino acid sequence having at least 90% identity to SEQ ID NO: 7 or SEQ ID NO: 9, wherein the substrate comprises Reb E, stevioside, or combinations thereof.

2. The method of claim 1, further comprising incubating a recombinant sucrose synthase with the substrate and the recombinant polypeptide.

3. The method of claim 1, wherein the recombinant polypeptide comprises an amino acid sequence having at least 95% identity to SEQ ID NO: 7.

4. The method of claim 3, wherein the recombinant polypeptide comprises the amino acid sequence of SEQ ID NO: 7.

5. The method of claim 1, wherein the recombinant polypeptide comprises an amino acid sequence having at least 95% identity to SEQ ID NO: 9.

6. The method of claim 5, wherein the recombinant polypeptide comprises the amino acid sequence of SEQ ID NO: 9.

7. The method of claim 1, wherein the substrate further comprises sucrose, uridine diphosphate (UDP), uridine diphosphate glucose (UDP-glucose), or combinations thereof.

8. The method of claim 1, further comprising incubating an HV1 enzyme with the substrate and the recombinant polypeptide.

9. The method of claim 2, wherein the sucrose synthase is selected from the group consisting of an *Arabidopsis* sucrose synthase 1, an *Arabidopsis* sucrose synthase 3 and a *Vigna radiate* sucrose synthase.

10. The method of claim 9, wherein the sucrose synthase is an *Arabidopsis thaliana* sucrose synthase 1.

11. The method of claim 1, wherein the Reb D4 produced is greater than 70% pure.

12. A method for synthesizing rebaudioside D4 from rebaudioside E, the method comprising:

preparing a reaction mixture comprising rebaudioside E, a substrate selected from the group consisting of sucrose, uridine diphosphate (UDP) and uridine diphosphate glucose (UDP-glucose), and C1m2, and incubating the reaction mixture for a sufficient time to produce rebaudioside D4, wherein a glucose is covalently coupled to the rebaudioside E to produce rebaudioside D4.

13. The method of claim 12 further comprising adding a HV1 enzyme to the reaction mixture.

14. A method for synthesizing rebaudioside D4 from rebaudioside E, the method comprising:

preparing a reaction mixture comprising rebaudioside E, a substrate selected from the group consisting of sucrose, uridine diphosphate (UDP) and uridine diphosphate glucose (UDP-glucose), and C1m3, and incubating the reaction mixture for a sufficient time to produce rebaudioside D4, wherein a glucose is covalently coupled to the rebaudioside E to produce rebaudioside D4.

15. The method of claim 14 further comprising adding a HV1 enzyme to the reaction mixture.

* * * * *